(12) United States Patent
Ge et al.

(10) Patent No.: US 8,039,484 B2
(45) Date of Patent: Oct. 18, 2011

(54) ANTIDIABETIC BICYCLIC COMPOUNDS

(75) Inventors: Min Ge, Edison, NJ (US); Songnian Lin, Monroe, NJ (US); Shawn P. Walsh, Bridgewater, NJ (US); Lihu Yang, Edison, NJ (US); Changyou Zhou, Princeton, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 310 days.

(21) Appl. No.: 12/441,733

(22) PCT Filed: Oct. 26, 2007

(86) PCT No.: PCT/US2007/022650
§ 371 (c)(1),
(2), (4) Date: Mar. 18, 2009

(87) PCT Pub. No.: WO2008/054675
PCT Pub. Date: May 8, 2008

(65) Prior Publication Data
US 2010/0105725 A1    Apr. 29, 2010

Related U.S. Application Data

(60) Provisional application No. 60/855,727, filed on Oct. 31, 2006.

(51) Int. Cl.
| | |
|---|---|
| *A61K 31/47* | (2006.01) |
| *A61K 31/192* | (2006.01) |
| *A61K 31/277* | (2006.01) |
| *C07D 487/02* | (2006.01) |
| *C07D 217/24* | (2006.01) |
| *C07D 213/36* | (2006.01) |
| *C07D 209/34* | (2006.01) |
| *C07D 311/34* | (2006.01) |
| *C07D 333/56* | (2006.01) |

(52) U.S. Cl. ........ 514/309; 514/345; 514/383; 514/393; 514/418; 514/443; 514/456; 514/521; 514/568; 546/141; 546/290; 548/262.4; 548/302.1; 548/512

(58) Field of Classification Search ........................ None
See application file for complete search history.

(56) References Cited

U.S. PATENT DOCUMENTS 7,759,493 B2 * 7/2010 Ge et al. .......................... 548/183
2003/0181494 A1    9/2003 Neogi et al.
2005/0171104 A1 * 8/2005 Rahimi-Ghadim et al. .. 514/241

OTHER PUBLICATIONS

Shinkai, "Novel antidiabetic agents", Exp. Opin Ther. Patents (2000), vol. 10, pp. 59-66.
Supplementary European Search Report re EP 07839789, dated Nov. 2, 2010.

* cited by examiner

*Primary Examiner* — Kamal Saeed
(74) *Attorney, Agent, or Firm* — Philippe L. Durette; Heidi M. Struse

(57) ABSTRACT

Diaryl ethers in which one of the aryl groups is a phenyl fused to a cycloalkyl or heterocyclic ring, to which is attached an acetic acid group, are agonists of G-protein coupled receptor 40 (GPR40) and are useful as therapeutic compounds, particularly in the treatment of Type 2 diabetes mellitus, and of conditions that often accompany this disease, including insulin resistance, obesity and lipid disorders.

14 Claims, No Drawings

ANTIDIABETIC BICYCLIC COMPOUNDS

CROSS REFERENCE TO RELATED APPLICATIONS

This application is the National Stage of International Application No. PCT/US2007/022650, filed 26 Oct. 2007, which claims the benefit under 35 U.S.C. 119(e) of U.S. Provisional Application No. 60/855,727, filed 31 Oct. 2006.

FIELD OF THE INVENTION

The instant invention is concerned with diaryl ether compounds in which one of the aryl groups is fused to a cycloalkyl or heterocyclic ring that is connected to an acetic acid moiety, including pharmaceutically acceptable salts and prodrugs thereof. The compounds are agonists of G-protein coupled receptor 40 (GPR40) and are useful as therapeutic compounds, particularly in the treatment of Type 2 diabetes mellitus, and of conditions that often accompany this disease, including insulin resistance, obesity and lipid disorders.

BACKGROUND OF THE INVENTION

Diabetes is a disease derived from multiple causative factors and characterized by elevated levels of plasma glucose (hyperglycemia) in the fasting state or after administration of glucose during an oral glucose tolerance test. There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin-dependent diabetes mellitus (NIDDM), insulin is still produced in the body. Patients having type 2 diabetes have a resistance to the effects of insulin in stimulating glucose and lipid metabolism in the main insulin-sensitive tissues, which are muscle, liver and adipose tissues. These patients often have normal levels of insulin, and may have hyperinsulinemia (elevated plasma insulin levels), as they compensate for the reduced effectiveness of insulin by secreting increased amounts of insulin. Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia that occurs with diabetes is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have several symptoms that together are referred to as syndrome X, or the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome, whether or not they have or develop overt diabetes mellitus, have an increased risk of developing the macrovascular and microvascular complications that occur with type 2 diabetes, such as atherosclerosis and coronary heart disease.

There are several available treatments for type 2 diabetes, each of which has its own limitations and potential risks. Physical exercise and a reduction in dietary intake of calories often dramatically improve the diabetic condition and are the usual recommended first-line treatment of type 2 diabetes and of pre-diabetic conditions associated with insulin resistance. Compliance with this treatment is very poor because of well-entrenched sedentary lifestyles and excess food consumption, especially of foods containing high amounts of fat and carbohydrates. Pharmacologic treatments have focused on three areas of pathophysiology: (1) Hepatic glucose production (biguanides), (2) insulin resistance (PPAR agonists), and (3) insulin secretion.

The biguanides are a class of drugs that are widely used to treat type 2 diabetes. The two best known biguanides, phenformin and metformin, cause some correction of hyperglycemia. The biguanides act primarily by inhibiting hepatic glucose production, and they also are believed to modestly improve insulin sensitivity. The biguanides can be used as monotherapy or in combination with other anti-diabetic drugs, such as insulin or an insulin secretagogues, without increasing the risk of hypoglycemia. However, phenformin and metformin can induce lactic acidosis and nausea/diarrhea. Metformin has a lower risk of side effects than phenformin and is widely prescribed for the treatment of Type 2 diabetes.

The glitazones (i.e. 5-benzylthiazolidine-2,4-diones) are a newer class of compounds that can ameliorate hyperglycemia and other symptoms of type 2 diabetes. The glitazones that are currently marketed (rosiglitazone and pioglitazone) are agonists of the peroxisome proliferator activated receptor (PPAR) gamma subtype. The PPAR-gamma agonists substantially increase insulin sensitivity in muscle, liver and adipose tissue in several animal models of type 2 diabetes, resulting in partial or complete correction of elevated plasma glucose levels without the occurrence of hypoglycemia. PPAR-gamma agonism is believed to be responsible for the improved insulin sensitization that is observed in human patients who are treated with the glitazones. New PPAR agonists are currently being developed. Many of the newer PPAR compounds are agonists of one or more of the PPAR alpha, gamma and delta subtypes. Compounds that are agonists of both the PPAR alpha and PPAR gamma subtypes (PPAR alpha/gamma dual agonists) are promising because they reduce hyperglycemia and also improve lipid metabolism. The currently marketed PPAR gamma agonists are modestly effective in reducing plasma glucose and HemoglobinA1C. The currently marketed compounds do not greatly improve lipid metabolism and may actually have a negative effect on the lipid profile. Thus, the PPAR compounds represent an important advance in diabetic therapy, but further improvements are still needed.

Another widely used drug treatment involves the administration of insulin secretagogues, such as the sulfonylureas (e.g. tolbutamide and glipizide). These drugs increase the plasma level of insulin by stimulating the pancreatic β-cells to secrete more insulin. Insulin secretion in the pancreatic β-cell is under strict regulation by glucose and an array of metabolic, neural and hormonal signals. Glucose stimulates insulin production and secretion through its metabolism to generate ATP and other signaling molecules, whereas other extracellular signals act as potentiators or inhibitors of insulin secretion through GPCR's present on the plasma membrane. Sulfonylureas and related insulin secretagogues act by blocking the ATP-dependent K+ channel in β-cells, which causes depolarization of the cell and the opening of the voltage-dependent Ca2+ channels with stimulation of insulin release. This mechanism is non-glucose dependent, and hence insulin secretion can occur regardless of the ambient glucose levels. This can cause insulin secretion even if the glucose level is low, resulting in hypoglycemia, which can be fatal in severe cases. The administration of insulin secretagogues must therefore be carefully controlled. The insulin secretagogues are often used as a first-line drug treatment for Type 2 diabetes.

There has been a renewed focus on pancreatic islet-based insulin secretion that is controlled by glucose-dependent insulin secretion. This approach has the potential for stabilization and restoration of β-cell function. In this regard, several orphan G-protein coupled receptors (GPCR's) have recently been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 (Itoh, Y. et al., Nature. 422: 173 [2003]; Briscoe, C. P. et al., J. Biol. Chem. 278: 11303 [2003]; Kotarsky, K. et al., Biochem. Biophys. Res. Comm. 301: 406 [2003]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a potential target for the treatment of type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be highly advantageous, because long term diabetes therapy often leads to the gradual diminution of islet activity, so that after extended periods of treatment, it is often necessary to treat type 2 diabetic patients with daily insulin injections. By restoring or preserving islet function, GPR40 agonists may delay or prevent the diminution and loss of islet function in a type 2 diabetic patient.

SUMMARY OF THE INVENTION

The class of compounds described herein is a new class of GPR40 agonists. The compounds are useful in the treatment of diseases that are modulated by GPR40 agonists, including type 2 diabetes and hyperglycemia that may be associated with type 2 diabetes or pre-diabetic insulin resistance.

The present invention is directed to a compound of formula I, or a pharmaceutically acceptable salt thereof, including individual diastereomers and enantiomers, and mixtures of diastereomers and/or enantiomers:

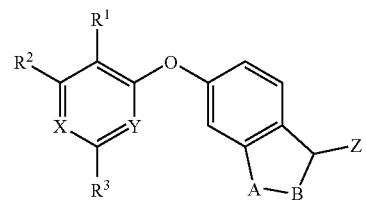

In the compound of Formula I, A is selected from the group consisting of —$CH_2$—, —$CF_2$—, —O—, —$N(R^6)$—, —S—, —S(O)—, —$S(O)_2$—, —C(=O)—, and —CH(OH)—; and B is selected from —$CH_2$—, —$CH_2CH_2$—, and —CH($CH_3$)—;

or alternatively -A-B- is —$N(R^6)C(=O)$— or —C(=O)$N(R^6)$—, or -A-B- represents two atoms that are connected to form one side of a 5-membered heteroaromatic ring having 1-3 heteroatoms independently selected from O, N and S, where the 5-membered heteroaromatic ring is optionally substituted with 1-3 groups independently selected from halogen, $CH_3$, $CF_3$, —$OCH_3$, and —$OCF_3$;

X is selected from =$C(R^4)$— and =N—; and Y is selected from =$C(R^5)$— and =N—; with the proviso that X and Y are not both =N—;

Z is —$CR^7R^8CO_2R^9$;

Heterocycle is a 5-6 membered saturated or partly saturated monocyclic heterocyclic ring having 1-3 heteroatoms independently selected from O, N and S;

Heteroaryl is a 5-6 membered monocyclic heteroaromatic ring having 1-3 heteroatoms independently selected from O, N and S;

$R^1$, $R^2$, $R^3$, $R^4$, and $R^5$ are each independently selected from the group consisting of H, halogen, —CN, —$NO_2$, —$C_1$-$C_6$alkyl, —$OC_1$-$C_6$alkyl, —$SC_1$-$C_6$alkyl, —$S(O)_2C_1$-$C_6$alkyl, —$N(R^6)(R^6)$, —$N(R^6)C(=O)C_1$-$C_6$alkyl, —$N(R^6)S(O)_2C_1$-$C_6$alkyl, —C(=O)H, —C(=O)OH, —C(=O)OC$_1$-$C_6$alkyl, —C(=O)$C_1$-$C_6$alkyl, —C(=O)$N(R^6)(R^6)$, PhenylCH=CHC(=O)—, PhenylC(=O)CH=CH—, —C(=O)Phenyl, —C(=O)Naphthyl, —C(=O)Heterocyle, Heterocycle, Heteroaryl, $C_3$-$C_7$Cycloalkyl, Phenyl and Naphthyl;

wherein —$C_1$-$C_6$alkyl and the alkyl groups of —$OC_1$-$C_6$alkyl, —$SC_1$-$C_6$alkyl, —$S(O)_2C_1$-$C_6$alkyl, —$N(R^6)C(=O)C_1$-$C_6$alkyl, —$N(R^6)S(O)_2C_1$-$C_6$alkyl, —C(=O)$OC_1$-$C_6$alkyl, and —C(=O)$C_1$-$C_6$alkyl are optionally substituted with 1-5 halogens and optionally substituted with 1-2 groups independently selected from —OH, —$OC_1$-$C_3$alkyl optionally substituted with 1-5 halogens, —$S(O)_2C_1$-$C_3$alkyl, —C(=O)$C_1$-$C_3$alkyl, —$OC(=O)C_1$-$C_3$alkyl, —NHC(=O)$CH_3$, —NHC(=O)$OC_1$-$C_6$alkyl, —$NHS(O)_2CH_3$, —$N(R^6)(R^6)$, Heterocycle, Heteroaryl, $C_3$-$C_7$Cycloalkyl, Phenyl, and Naphthyl;

wherein Phenyl of PhenylCH=CHC(=O)—, Phenyl of PhenylC(=O)CH=CH—, —C(=O)Phenyl, —C(=O)Naphthyl, —C(=O)Heterocyle, Heterocycle, Heteroaryl, $C_3$-$C_7$Cycloalkyl, Phenyl and Naphthyl either as $R^1$, $R^2$, $R^3$, $R^4$, and $R^5$ or as substituents on $R^1$, $R^2$, $R^3$, $R^4$, and $R^5$ are optionally substituted with 1-4 substituents independently selected from halogen, —CN, —NO$_2$, —OH, —C$_1$-C$_3$alkyl, —C(=O)C$_1$-C$_3$alkyl, —S(O)$_2$C$_1$-C$_3$alkyl, and —OC$_1$-C$_3$alkyl, wherein the —C$_1$-C$_3$alkyl, —OC$_1$-C$_3$alkyl, —S(O)$_2$C$_1$-C$_3$alkyl, and —C(=O)C$_1$-C$_3$alkyl substituents are optionally substituted with 1-5 halogens;

wherein optionally the pair of substituents $R^1$ and $R^2$ together represent a 3- or 4-carbon bridging group selected from —CH$_2$CH$_2$CH$_2$—, —CH$_2$CH$_2$CH$_2$CH$_2$—, and —CH=CH—CH=CH—, forming a fused cyclopentyl, cyclohexyl, or phenyl ring at the $R^1$ and $R^2$ positions, wherein said bridging group is optionally substituted with 1-3 groups independently selected from halogen, —OH, —CN, —NO$_2$, —C$_1$-C$_3$alkyl, —OC$_1$-C$_3$alkyl, —SC$_1$-C$_3$alkyl, —S(O)$_2$C$_1$-C$_3$alkyl, —CF$_3$, and —OCF$_3$;

Each $R^6$ is independently selected from the group consisting of H and —C$_1$-C$_6$alkyl;

$R^7$ is selected from the group consisting of H and —C$_1$-C$_3$alkyl;

$R^8$ is selected from the group consisting of H, —OH, —C$_1$-C$_3$alkyl optionally substituted with 1-3 halogens, and —OC$_1$-C$_3$alkyl optionally substituted with 1-3 halogens and optionally with one group —C(=O)OR$^{10}$; and $R^9$ and $R^{10}$ are independently selected from the group consisting of H and —C$_1$-C$_6$alkyl, wherein —C$_1$-C$_6$alkyl is optionally substituted with 1-5 halogens.

DETAILED DESCRIPTION OF THE INVENTION

The invention has numerous embodiments, which are summarized below. The invention includes the compounds as shown. It also includes individual diastereomers, enantiomers, and epimers of the compounds; mixtures of diastereomers and/or enantiomers; and racemates. The invention also includes pharmaceutically acceptable salts of the compounds, and pharmaceutical compositions comprising the compounds and a pharmaceutically acceptable carrier. The compounds are useful in treating type 2 diabetes and insulin resistance. The compounds may also be useful in treating or controlling obesity.

In the descriptions of the structures of the compounds, alkyl groups may be either linear or branched, unless otherwise defined.

A subgroup of the compounds of Formula I comprises compounds, including pharmaceutically acceptable salts thereof, in which $R^1$, $R^2$, $R^3$, $R^4$, and $R^5$ are independently selected from (1) H; (2) halogen; (3) —NO$_2$; (4) —CN; (5)-C$_{1-6}$alkyl, which is optionally substituted with 1-5 halogens and optionally substituted with 1-2 substituents independently selected from —OH, —C(=O)C$_1$-C$_3$alkyl, and —OC$_{1-3}$alkyl which is optionally substituted with 1-3 halogens; (6) —OC$_{1-6}$alkyl, which is optionally substituted with 1-5 halogens and optionally with one Phenyl; (7) —C(=O)C$_1$-C$_3$alkyl, which is optionally substituted with 1-5 halogens; (8) —N(R$^6$)(R$^6$); (9) —C(=O)N(R$^6$)(R$^6$); (10) —C(=O)OC$_1$-C$_3$alkyl; (11) —S(O)$_2$C$_1$-C$_3$alkyl; (12) Phenyl; (13) PhenylCH=CHC(=O)—; and (14) PhenylC(=O)CH=CH—; wherein Phenyl in all uses is optionally substituted with 1-3 groups independently selected from halogen, CH$_3$, CF$_3$, —OCH$_3$, and —OCF$_3$.

In subgroups of the compounds of Formula 1, or pharmaceutically acceptable salts thereof, each $R^6$ is independently selected from the group consisting of H and —C$_1$-C$_3$alkyl.

In subgroups of the compounds of Formula 1, or pharmaceutically acceptable salts thereof, $R^1$ and $R^2$ together represent the 4-carbon chain —CH=CH—CH=CH—, forming a fused phenyl ring at the $R^1$ and $R^2$ positions, wherein the fused phenyl ring is optionally substituted with 1-3 substituents independently selected from halogen, —OH, —CN, —NO$_2$, —C$_1$-C$_3$alkyl, —OC$_1$-C$_3$alkyl, —SC$_1$-C$_3$alkyl, —S(O)$_2$C$_1$-C$_3$alkyl, —CF$_3$, and —OCF$_3$.

In subgroups of the compounds of Formula 1, or pharmaceutically acceptable salts thereof, $R^1$, $R^2$, $R^3$, $R^4$ and $R^5$ are each independently selected from H, halogen, C$_1$-C$_5$alkyl optionally substituted with 1-5F, —OC$_1$-C$_5$alkyl optionally substituted with 1-5F, —CH$_2$OH, —CH(OH)CH$_3$, —CH(OH)CF$_3$, —C(=O)H, —C(=O)CH$_3$, —CN, —NO$_2$, Phenyl, —OCH$_2$Phenyl, —C(=O)OC$_1$-C$_3$alkyl, —S(O)$_2$CH$_3$, —C(=O)N(R$^6$)(R$^6$), —N(R$_6$)(R$_6$), PhenylCH=CHC(=O)—, and PhenylC(=O)CH=CH—, wherein Phenyl in each instance is optionally substituted with 1-3 groups independently selected from halogen, CH$_3$, CF$_3$, —OCH$_3$, and —OCF$_3$.

In subgroups of the compound of Formula I, or a pharmaceutically acceptable salt thereof, $R^1$ and $R^2$ together represent the 4-carbon chain —CH=CH—CH=CH—, forming a fused phenyl ring at the $R^1$ and $R^2$ positions, wherein the fused phenyl ring is optionally substituted with 1-2 substituents independently selected from halogen, —C$_1$-C$_3$alkyl, —OC$_1$-C$_3$alkyl, —CF$_3$, and —OCF$_3$.

In subgroups of the compound of Formula I, or a pharmaceutically acceptable salt thereof, each R$_6$ group is independently selected from H and CH$_3$.

In subgroups of the compound of Formula I, or a pharmaceutically acceptable salt thereof, $R^1$ and $R^2$ together represent the 4-carbon chain —CH=CH—CH=CH—, forming a fused phenyl ring at the $R^1$ and $R^2$ positions, wherein the fused phenyl ring is optionally substituted with 1-3 substituents independently selected from halogen, —OH, —CN, —NO$_2$, —C$_1$-C$_3$alkyl, —OC$_1$-C$_3$alkyl, —SC$_1$-C$_3$alkyl, —S(O)$_2$C$_1$-C$_3$alkyl, —CF$_3$, and —OCF$_3$.

In subgroups of the compound of Formula I, or a pharmaceutically acceptable salt thereof, A is selected from —CH$_2$—, —CF$_2$—, —O—, —N(R$^6$)—, —S—, —S(O)—, —S(O)$_2$—, —C(=O)—, and —CH(OH)—.

In subgroups of the compound of Formula I, or a pharmaceutically acceptable salt thereof, B is selected from the group consisting of —CH$_2$—, —CH$_2$CH$_2$—, and —CH(CH$_3$)—.

In subgroups of the compound of Formula 1, or a pharmaceutically acceptable salt thereof, -A-B- is selected from the group consisting of —N(R$^6$)C(=O)—, —C(=O)N(R$^6$)—,

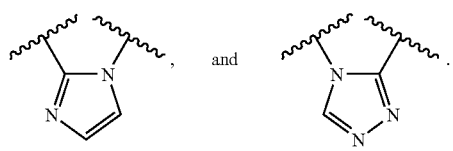

In subgroups of the compound of Formula I, or a pharmaceutically acceptable salt thereof, A is selected from the group consisting of —CH$_2$—, —O—, —S—, —S(O)$_2$—, —C(=O)—, and —CH(OH)—.

In subgroups of the compound of Formula 1, or a pharmaceutically acceptable salt thereof, Z is —CR$^7$R$^8$CO$_2$H; where $R^7$ is H;

$R^8$ is selected from the group consisting of H, —OH, CH$_3$, and —OCH$_2$C(=O)OR$^{10}$; and $R^{10}$ is selected from the group consisting of H and —C$_1$-C$_4$alkyl.

In a subgroup of the compound of Formula 1, or a pharmaceutically acceptable salt thereof, A is selected from —CH$_2$—, —O—, —S—, —S(O)$_2$—, —C(=O)—, and —CH(OH)—; and B is selected from —CH$_2$—, —CH$_2$CH$_2$—, and —CH(CH$_3$)—;

or alternatively -A-B- is selected from the group consisting of —N(R$^6$)C(=O)—, —C(=O)N(R$^6$)—,

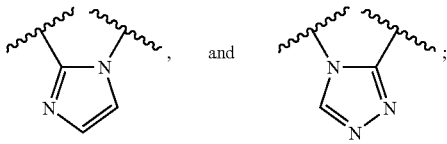

wherein R$^1$ is selected from the group consisting of H, halogen, C$_1$-C$_5$alkyl optionally substituted with 1-5F, —OC$_1$-C$_5$alkyl optionally substituted with 1-5F, —CH$_2$OH, —CH(OH)CH$_3$, —CH(OH)CF$_3$, —C(=O)H, —C(=O)CH$_3$, —CN, —NO$_2$, —C(=O)OCH$_3$, —S(O)$_2$CH$_3$, —C(=O)N(R$^6$)(R$^6$), —N(R$_6$)(R$_6$), and —OCH$_2$Phenyl in which Phenyl is optionally substituted with 1-3 groups independently selected from halogen, CH$_3$, CF$_3$, —OCH$_3$, and —OCF$_3$;

R$^2$ is selected from the group consisting of H, halogen, C$_1$-C$_3$alkyl optionally substituted with 1-3F, —OC$_1$-C$_3$alkyl optionally substituted with 1-3F, and Phenyl optionally substituted with 1-3 groups independently selected from halogen, CH$_3$, CF$_3$, —OCH$_3$, and —OCF$_3$;

R$^3$ is selected from H, halogen, CH$_3$, CF$_3$, —OCH$_3$, and —OCF$_3$;

R$^4$ is selected from H, halogen, CH$_3$, CF$_3$, —OCH$_3$, —OCF$_3$, C(=O)H, —C(=O)CH$_3$, —C(=O)OCH$_3$, —C(=O)N(R$^6$)(R$^6$), —CN, —NO$_2$, PhenylCH=CHC(=O)—, and PhenylC(=O)CH=CH—, wherein Phenyl in each instance is optionally substituted with 1-3 groups independently selected from halogen, CH$_3$, CF$_3$, —OCH$_3$, and —OCF$_3$;

R$^5$ is H;

Each R$_6$ is independently selected from H and CH$_3$;

wherein optionally R$^1$ and R$^2$ together represent the 4-carbon chain —CH=CH—CH=CH—, forming a fused phenyl ring at the R$^1$ and R$^2$ positions, wherein said fused phenyl ring is optionally substituted with 1-2 substituents independently selected from halogen, —C$_1$-C$_3$alkyl, —OC$_1$-C$_3$alkyl, —CF$_3$, and —OCF$_3$;

Z is —CR$^7$R$^8$CO$_2$H;

R$^7$ is H;

R$^8$ is selected from the group consisting of H, —OH, CH$_3$, and —OCH$_2$C(=O)OR$^{10}$; and R$^{10}$ is selected from the group consisting of H and —C$_1$-C$_4$alkyl.

In subsets of the compound of Formula I, or a pharmaceutically acceptable salt thereof, at least one of the groups R$^1$, R$^2$, R$^3$, R$^4$, or R$^5$ that is present is not H. In subsets of the compound of Formula I, or a pharmaceutically acceptable salt thereof, at least two of the groups R$^1$, R$^2$, R$^3$, R$^4$, and R$^5$ that are present are not H. In subsets of the compound of Formula I, or a pharmaceutically acceptable salt thereof, 2-3 of the groups R$^1$, R$^2$, R$^3$, R$^4$, and R$^5$ that are present are not H.

Although the specific stereochemistries described above are active, other stereoisomers, including diastereomers, enantiomers, epimers, and mixtures of these, including racemates, may also have utility in treating GPR40 mediated diseases. Inactive or less active diastereoisomers and enantiomers are also useful for scientific studies relating to the receptor and the mechanism of activation.

Structures of specific compounds and synthetic methods for making the compounds are disclosed in the Examples. In some cases, Examples are disclosed with analytical information, but without detailed synthetic information. Such compounds are readily made by one of ordinary skill of the art using the information in the specification.

The compounds of this invention may be used in pharmaceutical compositions comprising (a) the compound(s) or pharmaceutically acceptable salts thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of Formula I or a pharmaceutically acceptable salt thereof is the only active ingredient.

A compound of Formula I, or a pharmaceutically acceptable salt thereof, may be used in the manufacture of a medicament for the treatment of type 2 diabetes mellitus in a human or other mammalian patient.

A method of treating type 2 diabetes comprises the administration of a therapeutically effective amount of a compound of Formula I, or a pharmaceutically acceptable salt thereof, or a pharmaceutical composition comprising the compound, to a patient in need of treatment. Other medical uses of the compounds of Formula I are described hereinafter.

Definitions

"Ac" is acetyl, which is CH$_3$C(=O)—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. Cycloalkenyl rings comprise a double bond in the ring.

"Aryl" is commonly used to refer to carbocyclic aromatic structures. The most common aryl groups are phenyl and naphthyl. Phenyl is generally the most preferred aryl group.

"Heterocycle" means a fully or partially saturated 5-6-membered ring containing 1-3 heteroatoms independently selected from N, S and O. Examples of heterocycles include tetrahydrofuran, piperazine, piperidine, and morpholine.

"Heteroaryl" means a 5-6-membered aromatic ring containing 1-3 heteroatoms independently selected from N, O and S. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, and pyrazinyl.

"Halogen" includes fluorine, chlorine, bromine and iodine.

"Me" represents methyl.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers—Diastereomers—Geometric Isomers—Tautomers

Compounds of Formula I may contain one or more asymmetric centers and can thus occur as racemates, racemic mixtures, single enantiomers, individual diastereomers, and mixtures of diastereomers and/or enantiomers. The present invention is meant to comprehend all such isomeric forms of the compounds of Formula I. Specifically, the compounds of the instant invention have at least one asymmetric center, which is on the ring that is fused to the phenyl ring at the point where the acetic acid moiety is attached. There may also be a second asymmetric center on substituent groups. Each such asymmetric center will independently produce two optical isomers, and it is intended that all of the possible optical isomers, stereoisomers, and diastereomers in mixtures and as pure or partially purified compounds are included within the scope of this invention (i.e. all possible combinations of the asymmetric centers as pure compounds or in mixtures).

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, or when it has a basic substituent group in its structure, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are compounds of this invention. The claimed chemical structures of this application in some cases may themselves be prodrugs.

Utilities

Compounds of the present invention are potent agonists of the GPR40 receptor. The compounds of the invention, and pharmaceutically acceptable salts thereof, may be efficacious in the treatment of diseases that are modulated by GPR40 ligands and agonists. Many of these diseases are summarized below.

One or more of the following diseases may be treated by the administration of a therapeutically effective amount of a compound of this invention, or a pharmaceutically acceptable salt thereof, to a patient in need of treatment. Also, the compounds of the invention may be used for the manufacture of a medicament for treating one or more of these diseases:

(1) non-insulin dependent diabetes mellitus (type 2 diabetes);

(2) hyperglycemia;

(3) the metabolic syndrome;

(4) obesity;

(5) hypercholesterolemia;

(6) hypertriglyceridemia (elevated levels of triglyceride-rich-lipoproteins);

(7) mixed or diabetic dyslipidemia;

(8) low HDL cholesterol;

(9) high LDL cholesterol;

(10) hyperapoBliproteinemia; and

(11) atherosclerosis.

Preferred uses of the compounds are for the treatment of one or more of the following diseases by administering a therapeutically effective amount to a patient in need of treatment. The compounds may be used for manufacturing a medicament for the treatment of one or more of these diseases:

(1) Type 2 diabetes, and specifically hyperglycemia;
(2) Metabolic syndrome;
(3) Obesity; and
(4) Hypercholesterolemia.

The compounds are expected to be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, and medicaments as described herein may also be effective in reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others.

By keeping hyperglycemia under control, the compounds may also be effective in delaying or preventing vascular restenosis and diabetic retinopathy.

The compounds of this invention may also have utility in improving or restoring β-cell function, so that they may be useful in treating type 1 diabetes or in delaying or preventing a patient with type 2 diabetes from needing insulin therapy.

The compounds generally may be efficacious in treating one or more of the following diseases: (1) type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure, and (19) insulin resistance.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of hypercholesterolemia, atherosclerosis, hyperlipidemia, hypertriglyceridemia, dyslipidemia, high LDL, and low HDL.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating or controlling diabetes mellitus and/or hyperglycemia or hypertriglyceridemia or other diseases for which compounds of Formula I are indicated, generally satisfactory results are obtained when the compounds of the present invention are administered at a daily dosage of from about 0.1 milligram to about 100 milligram per kilogram of animal body weight, preferably given as a single daily dose or in divided doses two to six times a day, or in sustained release form. For most large mammals, the total daily dosage is from about 1.0 milligrams to about 1000 milligrams. In the case of a 70 kg adult human, the total daily dose will generally be from about 1 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets or capsules. Examples of doses in tablets and capsules are 0.1 mg, 0.25 mg, 0.5 mg, 1 mg, 2 mg, 5 mg, 10 mg, 25 mg, 50 mg, 100 mg, 200 mg, 300 mg, 400 mg, and 500 mg. Other oral forms may also have the same or similar dosages.

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

In some instances, depending on the solubility of the compound or salt being administered, it may be advantageous to formulate the compound or salt as a solution in an oil such as a triglyceride of one or more medium chain fatty acids, a lipophilic solvent such as triacetin, a hydrophilic solvent (e.g. propylene glycol), or a mixture of two or more of these, also optionally including one or more ionic or nonionic surfactants, such as sodium lauryl sulfate, polysorbate 80, polyethoxylated triglycerides, and mono and/or diglycerides of one or more medium chain fatty acids. Solutions containing surfactants (especially 2 or more surfactants) will form emulsions or microemulsions on contact with water. The compound may also be formulated in a water soluble polymer in which it has been dispersed as an amorphous phase by such methods as hot melt extrusion and spray drying, such polymers including HPMCAS, HPMCS, and polyvinylpyrrolidinones.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of Formula I may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. In the treatment of patients who have type 2 diabetes, insulin resistance, obesity, metabolic syndrome, and co-morbidities that accompany these diseases, more than one drug is commonly administered. The compounds of this invention may generally be administered to a patient who is already taking one or more other drugs for these conditions.

When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different overlapping schedules. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) PPAR gamma agonists and selective PPAR gamma partial agonists (SPPARM's), including both glitazones and non-glitazones (e.g. troglitazone, pioglitazone, englitazone, MCC-555, rosiglitazone, balaglitazone, netoglitazone, T-131, LY-300512, and LY-818, and SPPARM's described in U.S. Pat. No. 6,525,083, WO 2004/020409, and WO 2004/020408);

(b) biguanides such as metformin and phenformin;

(c) protein tyrosine phosphatase-1B (PTP-1B) inhibitors;

(d) dipeptidyl peptidase IV (DP-IV) inhibitors, such as sitagliptin, saxagliptin, and vildagliptin;

(e) insulin or insulin mimetics;

(f) sulfonylureas such as tolbutamide, glimepiride, glipizide, and related materials;

(g) α-glucosidase inhibitors (such as acarbose);

(h) agents which improve a patient's lipid profile, such as (i) HMG-CoA reductase inhibitors (lovastatin, simvastatin, rosuvastatin, pravastatin, fluvastatin, atorvastatin, rivastatin, itavastatin, ZD-4522 and other statins), (ii) bile acid sequestrants (cholestyramine, colestipol, and dialkylaminoalkyl derivatives of a cross-linked dextran), (iii) niacin receptor agonists, nicotinyl alcohol, nicotinic acid, or a salt thereof, (iv) PPARα agonists such as fenofibric acid derivatives (gemfibrozil, clofibrate, fenofibrate and bezafibrate), (v) cholesterol absorption inhibitors, such as for example ezetimibe, (vi) acyl CoA:cholesterol acyltransferase (ACAT) inhibitors, such as avasimibe, (vii) CETP inhibitors, such as torcetrapib and compounds described in WO 2005/100298, WO 2006/014413, and WO2006/014357, and (viii) phenolic anti-oxidants, such as probucol;

(i) PPARα/γ dual agonists, such as muraglitazar, tesaglitazar, farglitazar, and JT-501;

(j) PPARδ agonists such as those disclosed in WO97/28149;

(k) antiobesity compounds such as fenfluramine, dexfenfluramine, phentiramine, subitramine, orlistat, neuropeptide Y5 inhibitors, Mc4r agonists, cannabinoid receptor 1 (CB-1) antagonists/inverse agonists, and $\beta_3$ adrenergic receptor agonists;

(l) ileal bile acid transporter inhibitors;
(m) agents intended for use in inflammatory conditions such as aspirin, non-steroidal anti-inflammatory drugs, glucocorticoids, azulfidine, and cyclo-oxygenase 2 selective inhibitors;
(n) glucagon receptor antagonists;
(o) GLP-1,
(p) GIP-1,
(q) GLP-1 analogs, such as exendins, for example exenatide (Byetta),
(r) Glucokinase activators;
(s) GPR 119 agonists;
(t) GPR120 agonists; and
(u) Hydroxysterol dehydrogenase-1 (HSD-1) inhibitors.

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, other PPAR agonists, PTP-1B inhibitors, DP-IV inhibitors, and anti-obesity compounds.

BIOLOGICAL ASSAYS

Generation of GPR40-Expressing Cells

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

FLIPR Assays

FLIPR (Fluorimetric Imaging Plate Reader, Molecular Devices) assays were performed to measure agonist-induced calcium mobilization of the stable clones. For the FLIPR assay, one day before assay, GPR40/CHO NFAT BLA cells were seeded into black-wall-clear-bottom 384-well plates (Costar) at 1.4×10e4 cells/20 μl medium/well. The cells were incubated with 20 μl/well of the assay buffer (HBSS, 0.1% BSA, 20 mM HEPES, 2.5 mM probenecid, pH 7.4) containing 8 μM fluo-4, AM, 0.08% pluronic acid at room temperature for 100 minutes. Fluorescence output was measured using FLIPR. Compounds were dissolved in DMSO and diluted to desired concentrations with assay buffer. 13.3 μl/well of compound solution was added.

EC50 activities were measured for the compounds using both the human and mouse GPR40 cell lines. The activities for the compounds herein are as follows: human FLIPR EC50: 0.012 to 40 μM; mouse FLIPR EC50: 0.39 to 40 μM. The preferred compounds have an EC50<10 μM.

Inositol Phosphate Turnover Assay

The assay is performed in 96-well format. HEK cells stably expressing human GPR40 are plated to be 60-80% confluent within 72 hours. After 72 hours, the plates are aspirated and the cells washed with inositol-free DMEM (ICN). The wash media is replaced with 150 uL of 3H-inositol labeling media (inositol-free media containing 0.4% human albumin or 0.4% mouse albumin, 1× pen/strep antibiotics, glutamine, 25 mM HEPES to which is added 3H-myo-inositol NEN #NET114A 1 mCi/mL, 25 Ci/mmol diluted 1:150 in loading media with a final specific radioactivity of 1 uCi/150 uL). Alternatively, the human and mouse albumin can be added after the overnight labeling step before the addition of LiCl.

The assay is typically run the next day after 18 hours labeling. On the day of the assay, 5 uL of 300 mM LiCl is added to all wells and incubated at 37 degrees for 20 mins. 0.75 uL of 200× compounds are added and incubated with the cells for 60 minutes at 37 degrees. The media is then aspirated off and the assay terminated with the addition of 60 uL 10 mM formic acid. The cells are lysed for 60 mins at room temperature. 15-30 uL of lysate is mixed with 70 uL/1 mg YSi SPA beads (Amersham) in clear bottom Isoplates. The plates are shaken for 2 hours at room temperature. Beads are allowed to settle and the plates are counted in the Wallac Microbeta.

In Vivo Studies

Male C57BL/6N mice (7-12 weeks of age) are housed 10 per cage and given access to normal diet rodent chow and water ad libitum. Mice are randomly assigned to treatment groups and fasted 4 to 6 hours. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 minutes after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

EXAMPLES

The following Examples are provided to illustrate the invention and are not to be construed as limiting the invention in any manner. The scope of the invention is defined by the appended claims.

Methods for preparing the compounds of this invention are illustrated in the following Examples. Syntheses of several Intermediates that are used for making the exemplified compounds are also provided. Starting materials are either commercially available or are made by known procedures in the literature or as illustrated. The present invention further includes methods for the preparation of compounds of formula I as defined above. Some examples may provide analytical information without detailed synthetic information. These examples can be readily made by one of ordinary skill in the art of organic synthesis based on the information disclosed herein.

Intermediate 1

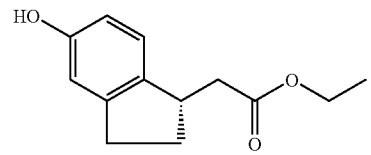

To a cooled (−78° C.) solution of ethyl [(1S)-5-methoxy-2,3-dihydro-1H-inden-1-yl]acetate (2.34 g, 10 mmol), prepared according to a published procedure (WO 2004/011446), in 50 mL of dichloromethane was added a solution of boron tribromide in dichloromethane (1.0 M, 35 mL, 35 mmol). The reaction was then warmed to RT for 30 min., then quenched with ice-water. The product was extracted with ethyl acetate twice. The organic phase was washed with water twice, dried with anhydrous sodium sulfate, and evaporated. The residue was dried under high vacuum to afford the desired compound, which was used in the next step without further purification. LC-MS: calc. for C13H16O3: 220 Found: 221 (M+H).

Intermediate 2

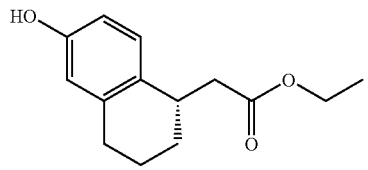

Step A

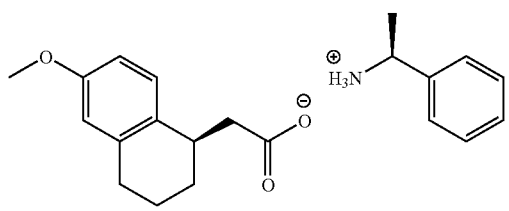

To a stirred solution of the racemic [6-methoxy-1,2,3,4-tetrahydronaphthalen-1-yl]acetic acid (69.4 g, prepared according to a published procedure (WO 2004/011446) in 1500 mL of acetone was added 38.7 mL of (S)-alpha-methylbenzylamine in one portion. The mixture was stirred at RT for 30 min, then 1500 mL of hexane was added. The mixture was stirred for one hour. The resulting solid was removed by filtration and washing with hexane/acetone (4:1 v/v), and was then dried in air to give the first batch of solid. The combined mother liquids were stored at 0-5° C. overnight. The resulting solid was collected by filtration to give a second batch of solid. The two batches of the salt were combined and then dissolved in a warm acetone (500 mL). 750 mL of hexane was added, and the mixture was stirred at RT for one hour. The resulting solid was collected by filtration, washed with hexane/acetone (4:1), and dried in air to give off-white crystals of (R,S)-salt.

Step B

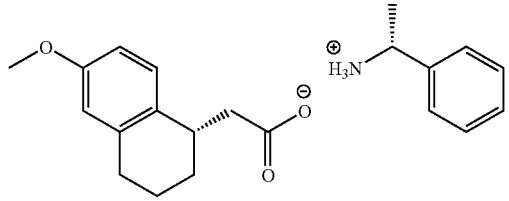

All mother liquids from the above step A were combined and condensed to give a light brown solid. 3N aq. HCl was added to adjust pH to <3. The mixture was stirred with ethyl acetate (500 mL) and the layers were separated. The organic phase was washed with 3N aq. HCl, dried over sodium sulfate, filtered and evaporated to afford a light brown solid (32 g, 145 mmol, S-enriched acid). This solid was dissolved in 500 mL of acetone, (R)-(+)-alpha-methylbenzylamine (16.6 mL, 145 mmol) was added, the mixture was refluxed until all the solid dissolved, and was then cooled to RT. The resulting precipitate was collected by filtration and washed with acetone to afford a white solid salt (S,R). The (S)-absolute configuration of the acid was confirmed by x-ray crystallography of the amide formed by treatment of the above salt with N-(3-Dimethylaminopropyl)-N'-ethylcarbodiimide hydrochloride (EDAC).

Step C

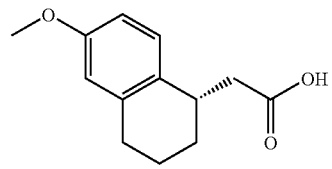

The (S,R) salt from the above step B (23.2 g) was stirred for one hour with 200 mL of 3N HCl and 200 mL of ethyl acetate. The organic phase was separated and washed with 3N aq. HCl (2×100 mL), dried over sodium sulfate, filtered and evaporated to give the desired (S)-acid as a light brown solid.

Step D

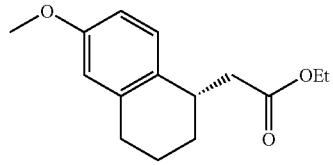

The (S)-acid from the above step D (14 g) was dissolved in 150 mL of ethanol, and 19 mL of trimethylsilyl chloride was added. The mixture was stirred at RT overnight, and was then evaporated and mixed with ethyl acetate (100 mL). The organic phase was washed with water and saturated aq. sodium hydrogen carbonate, dried over sodium sulfate, and purified by flash chromatography (Silica gel, 20% ethyl acetate/hexane) to give the desired (S)-ester as a colorless oil. 1H NMR (400 MHz, CDCl$_3$) δ 7.04 (d, J=7.7 Hz, 1H), 6.67 (m, 1H), 6.60 (m, 1H), 4.14 (m, 2H), 3.74 (bs, 3H), 3.26 (m, 1H), 2.80-2.40 (m, 4H), 1.90-1.60 (m, 4H), 1.24 (m, 3H).

Step E

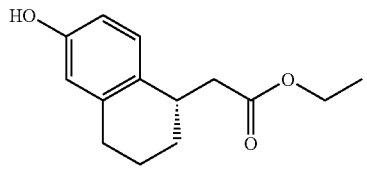

To a stirred, cold (−78° C.) solution of the product from the above step D (1.22 g, 4.92 mmol) in 25 mL of dichloromethane was added a solution of boron tribromide in dichloromethane (1.0 M, 20 mL, 20 mmol). The reaction was allowed to warm to 0° C. over 2 hours and allowed to stand at 0° C. for 40 minutes before being partitioned between EtOAc (100 mL) and water (100 mL). The aqueous layer was extracted with EtOAc (2×100 mL). The combined EtOAc layers were washed with water (100 mL), Brine (100 mL), dried over MgSO$_4$, filtered and concentrated to an oil. This material was dissolved in EtOH (10 mL), and 4 N HCl/dioxane (4 mL) was added. The solution was refluxed overnight and then concentrated in vacuo. The residue was dissolved in EtOAc (100 mL) and washed successively with aq. NaHCO$_3$ (50 mL), water (50 mL), and brine (50 mL). The organic layer was separated, dried over anhydrous Na$_2$SO$_4$, filtered, and concentrated in vacuo. The crude material was used as is. Rf=0.85 (50% EtOAc/hexane).

Intermediate 3

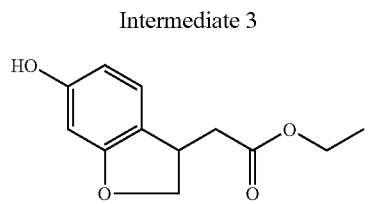

Step A

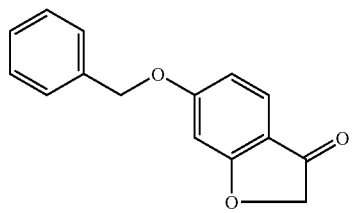

To 6-hydroxyl-2,3-dihydrobenzofuran-3-one (30 g, 200 mmol) in DMF (600 mL) was added K$_2$CO$_3$ (220 mmol, 30.4 g) followed by benzyl bromide (BnBr) (200 mmol, 24 mL). After stirring at room temperature for 3 hours, the reaction mixture was partitioned between methyl t-butyl ether (MTBE, 500 mL) and water (1 L). The aqueous layer was separated and further extracted with MTBE (2×500 mL). The organic layers were combined, washed with water (500 mL), Brine (500 mL), dried over anhydrous Na$_2$SO$_4$, filtered and concentrated in vacuo to give the desired compound. LC-MS calculated for C15H13O3 [M+H]: 241, found 241.

Step B

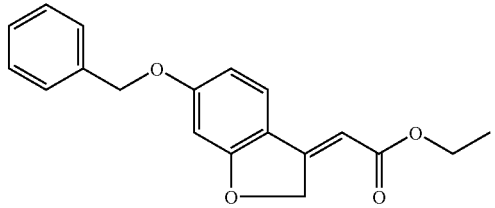

To a suspension of NaH (60% in mineral oil, 381 mmol, 15.2 g) in anhydrous THF (900 mL) was added triethyl phosphonoacetate (381 mmol, 76 mL) dropwise in an ice bath. After addition, the reaction was stirred at room temperature for 20 minutes until a clear solution was obtained. A solution of the ketone (45.7 g, 190 mmol) from Step A in THF (100 mL) was then added to the reaction. The reaction was stirred overnight at room temperature and then quenched with 0.1N HCl (1 L). The aqueous layer was separated and extracted with EtOAc (2×500 mL). The organic layers were combined, washed with water (500 mL), then Brine (500 mL), then dried over anhydrous Na$_2$SO$_4$, filtered, and concentrated in vacuo. The residue was purified by flash chromatography (10% to 30% EtOAc/hexanes) to give the desired compound. LC-MS calculated for C19H19O4 [M+H]: 311.1, found 311.3.

Step C

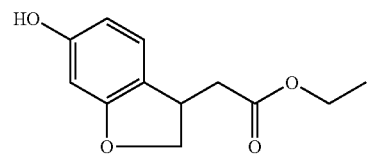

To a solution of the unsaturated ester (6.6 g, 21.3 mmol) from Step B in ethanol (75 mL) and EtOAc (75 mL) was added 10% Pd/C (2 g). The mixture was hydrogenated in a Parr shaker at 50 psi for 2 hours. The mixture was then filtered through celite. The filtrate was concentrated in vacuo to give the desired compound. LC-MS calculated for C12H15O4 [M+H]: 223, found 223.

Intermediate 4

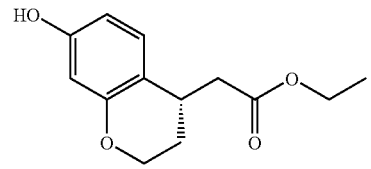

Step A

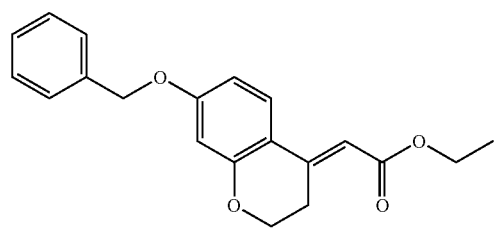

To a dried 3-neck 2 L round bottom was added freshly azeotroped 7-(benzyloxy)chroman-4-one (287 g, 1.13 mol, synthesized according to *J. Med. Chem.* 1998, 41, 1172-1184) and 2 L of anhydrous THF (no inhibitor). Zinc (124.9 g, 1.92 mol) and CuI (10.7 g, 56.5 mmol) were then quickly added to the reaction solution. After refluxing for 30 minutes under N$_2$ atmosphere, 81 mL of ethyl bromoacetate (½ of total needed, F.W. 167.01, d 1.506, 0.7 mol) was added dropwise to the refluxing mixture. Heat was then turned off and the reaction was stirred at ambient temperature for 4~5 h. Another 81 ml of ethyl bromoacetate (F.W. 167.01, d 1.506, 0.7 mol) was then added dropwise and the reaction was stirred without heating until the reaction temperature returned to ambient temperature. Solids were removed by vacuum filtration through celite and the filtrate was concentrated to ~800 mL by rotary evaporation. This was then poured into 1 L of 1N HCl (aq) with 1000 g of ice, and the mixture was stirred vigorously for 30 min. The mixture was extracted with EtOAc (1×2 L, 2×1 L). The combined organic layers were washed with $H_2O$ (1×3 L), Brine (1×2 L), dried over $Na_2SO_4$, and concentrated in vacuo. The crude compound was used without further purification.

Step B

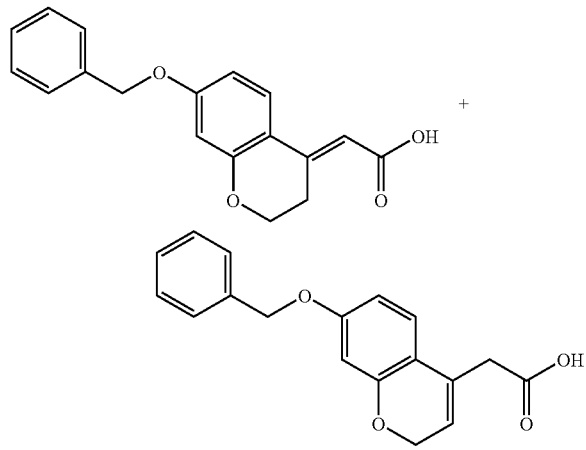

To a solution of crude product (~356 g, 1.1 mol) from step A in THF/MeOH/$H_2O$ (2:2:1, 2.5 L) was added LiOH monohydrate (92.4 g, M.W. 41.96, 2.2 mol). The reaction was stirred at ambient temperature overnight. The organic solvents were removed in vacuo and the residue was diluted with water to 3 L in volume. This aqueous solution was washed with diethyl ether (2×500 mL), and the aqueous layer was then acidified to pH=1 with 10 N HCl (aq). The solid was isolated by vacuum filtration, washed with EtOAc and dried under vacuum. The filtrate was extracted with EtOAc (2×500 mL). The combined organics were washed with brine (400 mL) and concentrated in vacuo. All solids were combined, triturated with minimal EtOAc, and dried under high vacuum to give a mixture of two isomers.

Step C

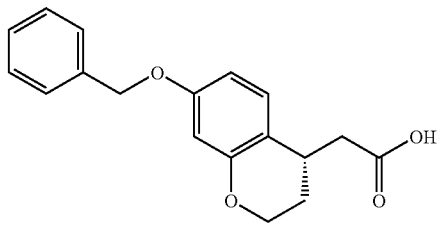

A solution of product from step B (20 g, 67.6 mmol) in anhydrous methanol (800 mL) was degassed by bubbling through $N_2$ for 1 hour. (R)-BINAP $RuCl_2$ (1.11 g, F.W. 794.65, 1.4 mmol) and 950 μL of freshly degassed triethylamine (F.W. 101.19, d 0.72, 6.76 mmol) were quickly added under $N_2$ atmosphere. The mixture was hydrogenated under $H_2$ (50 psi) for 4 days. The mixture was then filtered and the filtrate was concentrated in vacuo. The residue was purified by column chromatography to give the desired product (70% ee) and recovered starting material. The product was dissolved in minimal EtOAc (~20 mL) and petroleum ether (~20 mL) and re-crystallized to give chiral acid (~95% ee).

Step D

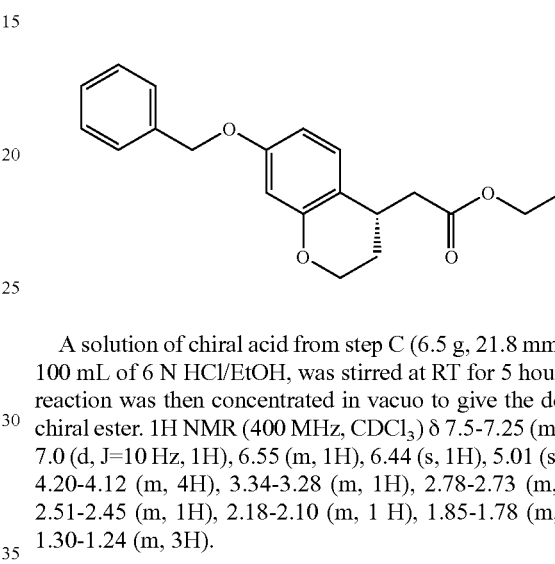

A solution of chiral acid from step C (6.5 g, 21.8 mmol) in 100 mL of 6 N HCl/EtOH, was stirred at RT for 5 hour. The reaction was then concentrated in vacuo to give the desired chiral ester. 1H NMR (400 MHz, $CDCl_3$) δ 7.5-7.25 (m, 5H), 7.0 (d, J=10 Hz, 1H), 6.55 (m, 1H), 6.44 (s, 1H), 5.01 (s, 2H), 4.20-4.12 (m, 4H), 3.34-3.28 (m, 1H), 2.78-2.73 (m, 1H), 2.51-2.45 (m, 1H), 2.18-2.10 (m, 1 H), 1.85-1.78 (m, 1H), 1.30-1.24 (m, 3H).

Step E

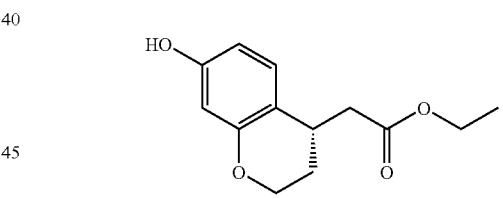

To the compound obtained in Step D (450 mg) in ethanol (10 mL) was added 10% Pd/C (500 mg). The mixture was hydrogenated under $H_2$ (1 atm) for 1 hour and then filtered through a pad of celite. The filtrate was concentrated in vacuo to give the desired product. LCMS for C13H16O4: calc. 236.1, observed 237.4 [M+H].

Intermediate 5

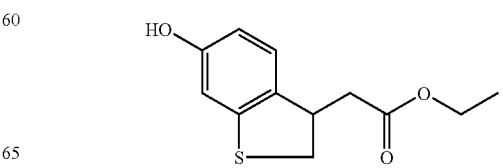

Step A

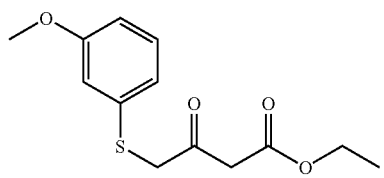

To a cooled (0° C.) solution of 3-methoxybenzenethiol (5.6 g, 40 mmol) in DMF (40 mL) was added NaH (1.76 g, 60% in mineral oil, 44 mmol), and the mixture was warmed to room temperature over 30 min. Ethyl 4-chloroacetoacetate (6.58 g, 40 mmol) was added dropwise at room temperature, and the reaction mixture was stirred for 17 hours at room temperature. The mixture was diluted with ethyl acetate, washed with water, and the aqueous layer was extracted with ethyl acetate (2×). Combined organic layers were dried with MgSO$_4$, filtered, and concentrated to afford the desired compound, which was used in the next step without further purification.

Step B

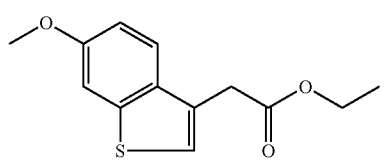

A mixture of celite (18 g), phosphorus pentoxide (3.6 g), and polyphosphoric acid (35 g) in anhydrous toluene (300 mL) was stirred for 30 min at 120° C. To this mixture was added the material obtained in Step A in toluene (5 mL), and the mixture was stirred for 70 min at 120° C. The reaction mixture was cooled to room temperature, filtered, and concentrated. The residue was purified by silica gel column chromatography using ethyl acetate/hexanes (5-25%) as the eluant to afford the desired product. LCMS for C13H14O3S: calc. 250, observed 251 [M+H].

Step C

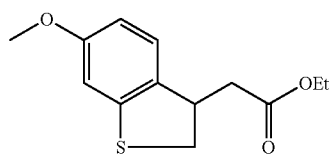

Ethyl (6-methoxy-1-benzothien-3-yl)acetate obtained in Step B (4.95 g, 19.8 mmol) was heated together with triethylsilane (9.5 mL) and trifluoroacetic acid (23 mL) for 4 hours at 75° C., then continued overnight. All volatiles were removed, and the residue was purified by silica gel column chromatography using ethyl acetate/hexanes (5-25%) as the eluant to afford the desired product. LCMS for C13H16O3S: calc. 252, observed 207 [M-OEt].

Step D

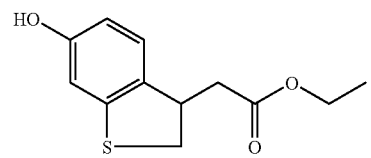

The desired compound was obtained following a procedure similar to that of Intermediate 1, using the material obtained in Step C. LCMS for C12H14O3S: calc. 238, observed 193 [M-OEt].

Intermediate 5a

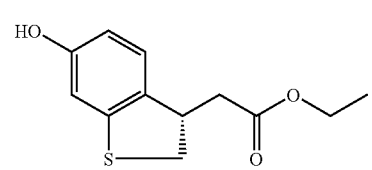

5a

Step A

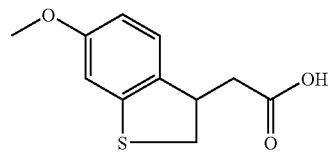

To a solution of the compound obtained in Step C of Intermediate 5 (4.76 g, 18.87 mmol) in EtOH (120 mL) was added a NaOH solution (22.6 mL, 2.5 N, 56.6 mmol), and the mixture was stirred for 22 h at room temperature. The reaction mixture was acidified with 2 N HCl, and extracted with ethyl acetate (2×), and the combined extracts were washed with brine, dried over MgSO$_4$, filtered, and concentrated to afford the desired compound. LCMS for C11H12O3S: calc. 224, observed 225 [M+H].

Step B

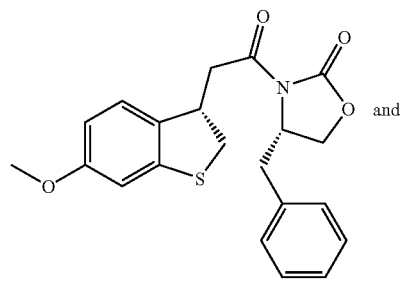

and

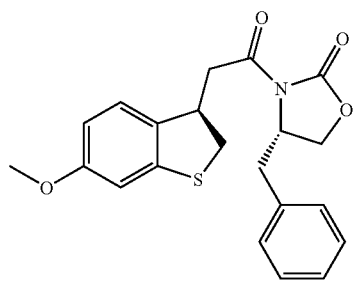

To a solution of the material obtained in Step A (3.99 g, 17.79 mmol) in THF (120 mL) were added Et$_3$N (7.5 mL, 53.37 mmol) and tert-butylacetyl chloride (2.79 g, 23.13 mmol), and the mixture was stirred for 1 h at room temperature. LiCl (1.13 g, 26.69 mmol) was added to the mixture, followed by addition of (S)-4-benzyl-2-oxazolidinone (4.73 g, 26.69 mmol), and the mixture was stirred for 3 days at room temperature. The mixture was diluted with ethyl acetate, washed with water, and the aqueous layer was extracted with ethyl acetate (2×). Combined organic layers were dried with MgSO$_4$, filtered, and concentrated. The residue was purified by silica gel column chromatography using ethyl acetate/hexanes (5-10%) as the eluant to afford the desired products. LCMS for C21H21NO4S: calc. 383, observed 384 [M+H].

Step C

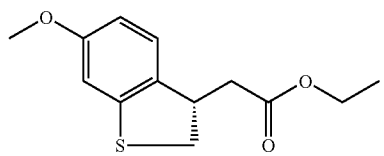

To a cooled (0° C.) solution of the lower Rf isomer obtained in Step B (1.5 g, 3.91 mmol) in THF/water (36 mL, 3/1) was added LiOH (3.91 mL, 2 N, 7.82 mmol), followed by dropwise addition of H$_2$O$_2$ (0.56 mL, 30%, 5.87 mmol). The mixture was stirred for an additional 70 min at 0° C. Na$_2$S$_2$O$_3$ (1.85 g) in water (20 mL) was added, and the mixture was stirred for 15 min before being diluted with ethyl acetate. The aqueous phase was acidified with HCl (2 N) to pH~2 and extracted with ethyl acetate (2×), and the combined organic layers were dried with MgSO$_4$, filtered, and concentrated. The residue was dissolved in EtOH (10 mL). A solution of HCl in dioxane (0.5 mL, 4 N) was added to the solution, and the mixture was stirred for 3 hours at 85° C. Solvent was removed, and the residue was purified by silica gel column chromatography using ethyl acetate/hexanes (10-40%) as the eluant to afford the desired product. LCMS for C13H16O3S: calc. 252, observed 207 [M-OEt].

Step D

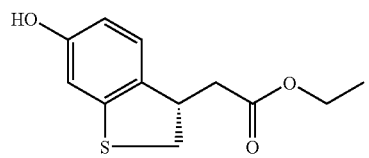

INTERMEDIATE 5a was prepared from material obtained in the above Step C using a procedure similar to that used in Step D of the preparation of INTERMEDIATE 5. LCMS for C12H14O3S: calc. 238, observed 193 [M-OEt].

Intermediate 5b

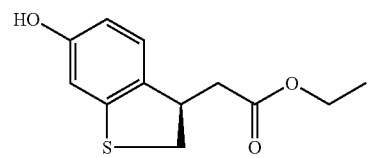

The desired compound was obtained following a procedure similar to that of Intermediate 5a, using the higher Rf material obtained in Step B of Intermediate 5a. LCMS for C12H14O3S: calc. 238, observed 193 [M-OEt].

Example 1

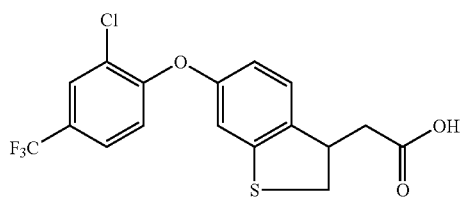

Step A

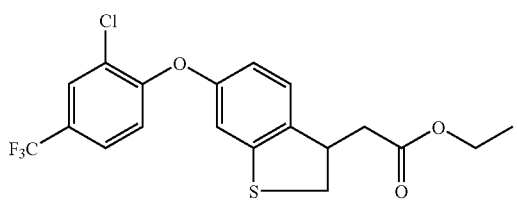

INTERMEDIATE 5 (350 mg, 1.47 mmol) was combined with 3-chloro-4-fluorobenzotrifluoride (349 mg, 01.76 mmol) and Cs$_2$CO$_3$ (1.20 g, 3.68 mmol) in 10 mL of N,N-dimethylformamide. The reaction mixture was stirred at 110° C. for 2 hours, then the solvent was removed, and water and ethyl acetate were added. The aqueous layer was acidified with 2N aq. HCl to pH~2. The ethyl acetate layer was separated and the aqueous layer was extracted with ethyl acetate (2×). Combined organic layers were dried with MgSO$_4$, filtered, and concentrated. The residue was purified by silica gel column chromatography using ethyl acetate/hexanes (5-20%) as the eluant to afford the desired product. LCMS for C19H16ClF3O3S: calc. 416, observed 417 [M+H].

Step B

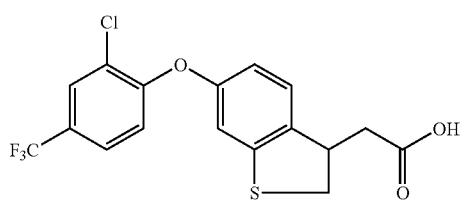

The material obtained from Step A was hydrolyzed to the desired acid following a procedure similar to the one described in Step A for the preparation of Intermediate 5a. LCMS for C17H12ClF3O3S: calc. 388, observed 387 [M−H].

Example 2

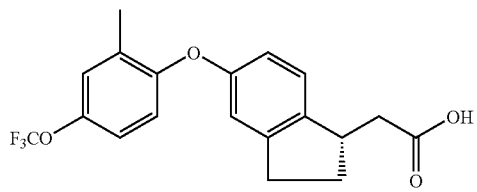

Step A

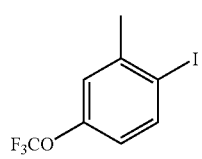

A mixture of 2-methyl-4-trifluoromethoxyaniline (1.0 g, 5.23 mmol), 15% sulfuric acid (10 mL), and ethanol (2 mL) was stirred at 0° C. Sodium nitrite (397 mg, 5.75 mmol) was added to this reaction mixture at 0° C. and the mixture was stirred for 5 h at the same temperature. Sodium iodide (1.02 g, 6.80 mmol) was then added at 0° C. The mixture was allowed to warm to room temperature and stirred at room temperature for 16 h. The reaction mixture was then extracted with ethyl acetate (30 mL×3). The combined organic layers were washed with an aqueous saturated sodium sulfite solution and brine, dried over magnesium sulfate, and concentrated. Silica gel column chromatography with ethyl acetate/hexanes (0-2%) as the eluant afforded the desired product.

Step B

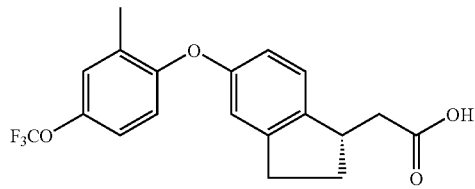

INTERMEDIATE 1 (25 mg, 0.11 mmol) was combined with 1-iodo-2-methyl-4-trifluoromethoxybenzene (51 mg, 0.17 mmol), copper (I) iodide (5.3 mg, 0.028 mmol), N,N-dimethylglycine hydrochloride salt (11.9 mg, 0.085 mmol), and Cs2CO3 (111 mg, 0.34 mmol) in 1.2 mL of anhydrous N,N-dimethylformamide/dioxane (3/1). The reaction tube was sealed, degassed, and backfilled with nitrogen twice, and the mixture was stirred at 110° C. for 24 hours. Solvents were removed, and water and ethyl acetate were added. The aqueous layer was acidified with 2N aq. HCl to pH~2. The ethyl acetate layer was separated, and the aqueous layer was extracted with ethyl acetate (2×). The combined organic layers were dried with MgSO4, filtered, and concentrated. The residue was purified by silica gel column chromatography using ethyl acetate/hexanes (25%) as the eluant to afford the desired product. LCMS for C21H21F3O4: calc. 394, observed 395 [M+H].

Step C

The material obtained from Step B was hydrolyzed to the desired acid following a procedure similar to the one described in Step B for the preparation of Example 1. LCMS for C19H17F3O4: calc. 366, observed 365 [M−H].

The following examples were prepared following procedures similar to those used in the preparation of Example 1 and Example 2, from their corresponding phenol and aryl halide precursors. These examples are shown in Table 1.

TABLE 1

| Example | Compound Structure | Molecular Formula | MW (calc.) | MW Observed |
|---|---|---|---|---|
| 3 | ![structure] | C18H14ClF3O3 | 370 | 369 [M − H] |
| 4 | ![structure] | C19H16ClF3O3 | 384 | 383 [M − H] |

TABLE 1-continued

| Example | Compound Structure | Molecular Formula | MW (calc.) | MW Observed |
|---|---|---|---|---|
| 5 | 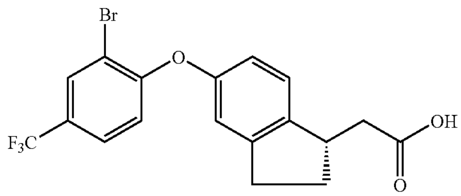 | C18H14BrF3O3 | 414 | 413 [M − H] |
| 6 | 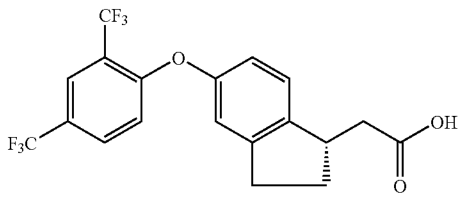 | C19H14F6O3 | 404 | 403 [M − H] |
| 7 | 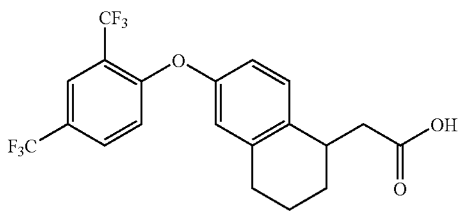 | C20H16F6O3 | 418 | 417 [M − H] |
| 8 | 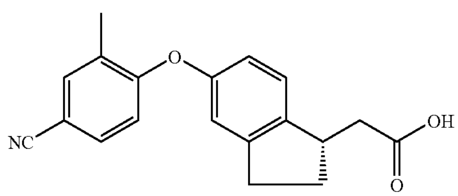 | C19H17NO3 | 307 | 308 [M + H] |
| 9 | 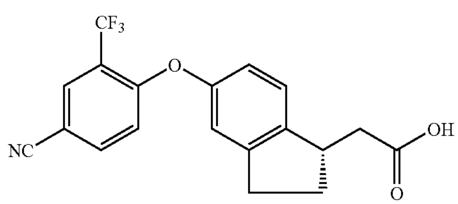 | C19H14F3NO3 | 361 | 362 [M + H] |
| 10 | 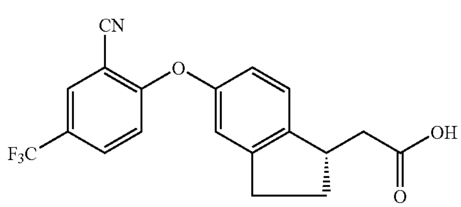 | C19H14F3NO3 | 361 | 362 [M + H] |
| 11 | 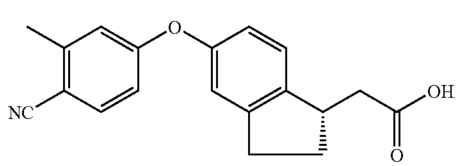 | C19H17NO3 | 307 | 308 [M + H] |

TABLE 1-continued

| Example | Compound Structure | Molecular Fomula | MW (calc.) | MW Observed |
|---|---|---|---|---|
| 12 | 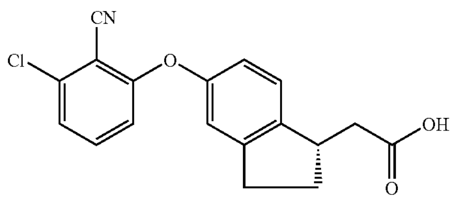 | C18H14ClNO3 | 327 | 328 [M + H] |
| 13 | 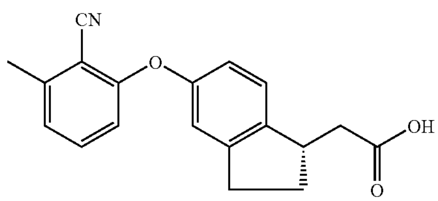 | C19H17NO3 | 307 | 308 [M + H] |
| 14 | 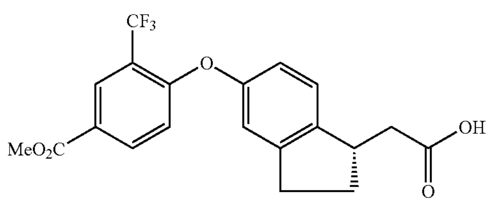 | C20H17F3O5 | 394 | 395 [M + H] |
| 15 | 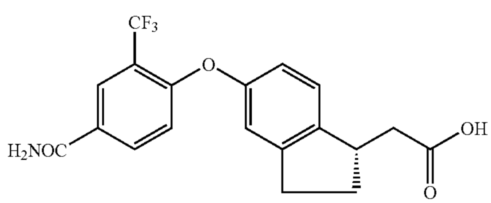 | C19H16F3NO4 | 379 | 380 [M + H] |
| 16 | 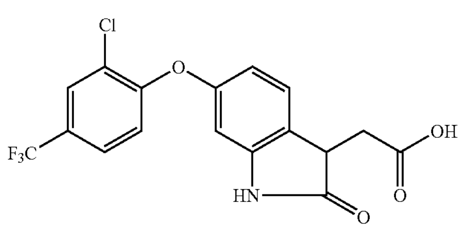 | C17H11ClF3NO4 | 385 | 386 [M + H] |
| 17 | 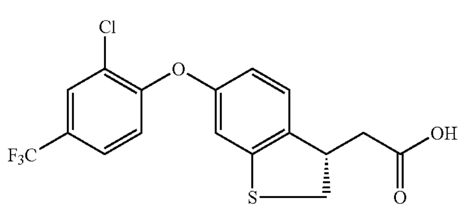 | C17H12ClF3O3S | 388 | 387 [M − H] |
| 18 | 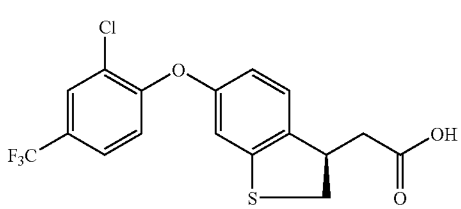 | C17H12ClF3O3S | 388 | 387 [M − H] |

TABLE 1-continued

| Example | Compound Structure | Molecular Fomula | MW (calc.) | MW Observed |
|---|---|---|---|---|
| 19 | 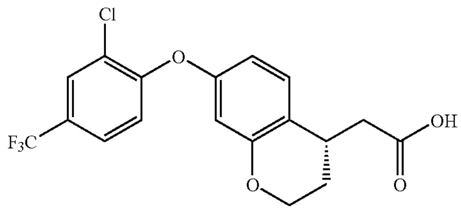 | C18H14ClF3O4 | 386 | 385 [M − H] |
| 20 | 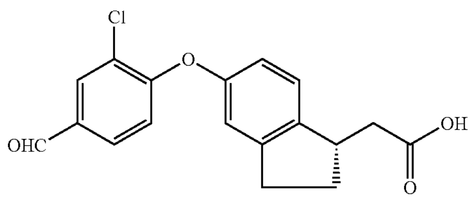 | C18H15ClO4 | 330 | 329 [M − H] |
| 21 | 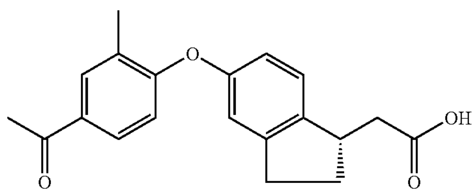 | C20H20O4 | 323 | [M − H] |
| 22 | 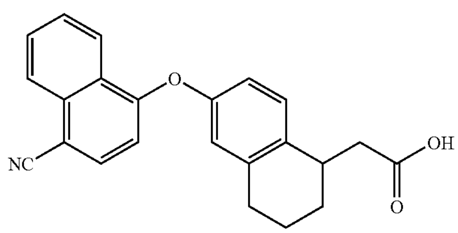 | C23H19NO3 | 357 | 356 [M − H] |
| 23 | 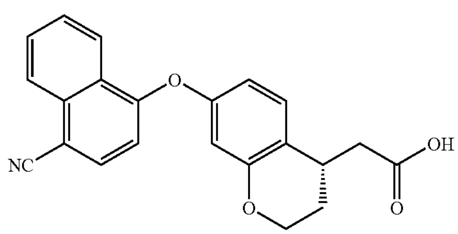 | C22H17NO4 | 359 | 358 [M − H] |
| 24 | 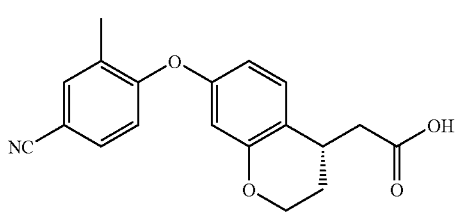 | C19H17NO4 | 322 | [M − H] |
| 25 | 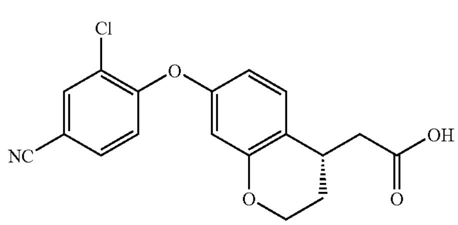 | C18H14ClNO4 | 342 | [M − H] |

TABLE 1-continued

| Example | Compound Structure | Molecular Fomula | MW (calc.) | MW Observed |
|---|---|---|---|---|
| 26 | 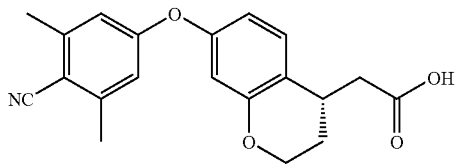 | C20H19NO4 | 336 | [M − H] |
| 27 | 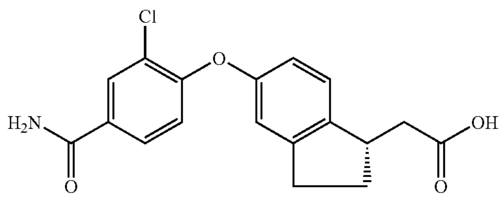 | C18H16ClNO4 | 345 | 344 [M − H] |
| 28 | 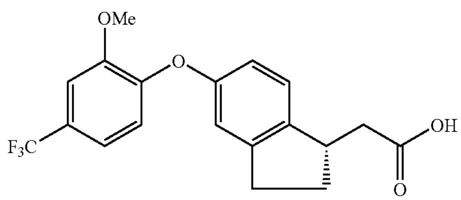 | C19H17F3O4 | 366 | 365 [M − H] |
| 29 | 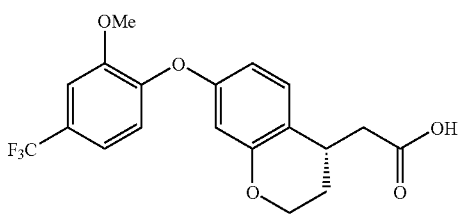 | C19H17F3O | 382 | 381 [M − H] |
| 30 | 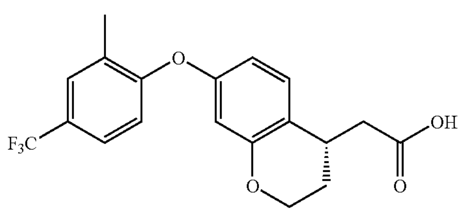 | C19H17F3O4 | 366 | 365 [M − H] |
| 31 | 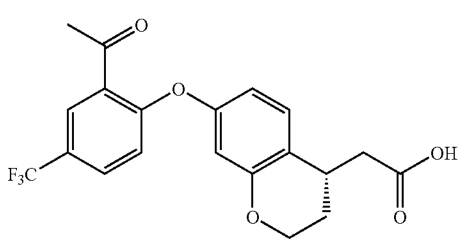 | C20H17F3O5 | 394 | 393 [M − H] |
| 32 | 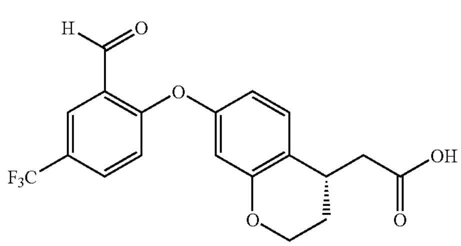 | C19H15F3O5 | 380 | 379 [M − H] |

TABLE 1-continued

| Example | Compound Structure | Molecular Formula | MW (calc.) | MW Observed |
|---|---|---|---|---|
| 33 | 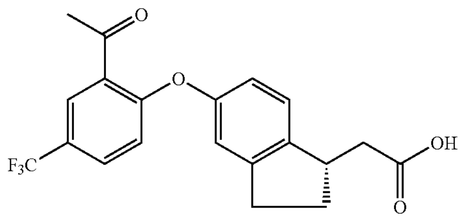 | C20H17F3O4 | 378 | 377 [M − H] |
| 34 | 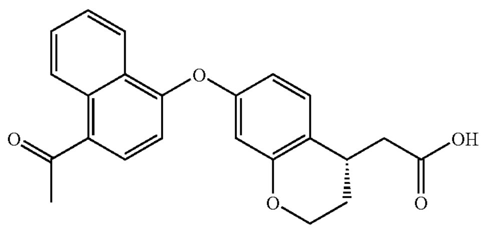 | C23H20O5 | 376 | 375 [M − H] |
| 35 | 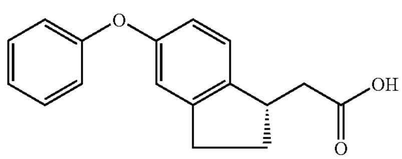 | C17H16O3 | 268 | 267 [M − H] |
| 36 | 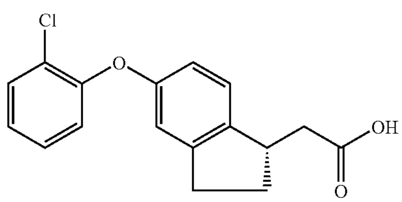 | C17H16ClO3 | 302 | 301 [M − H] |
| 37 | 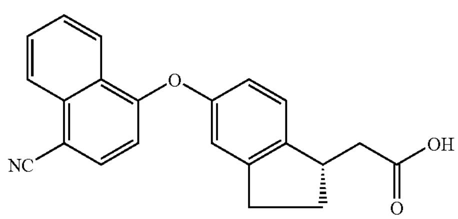 | C22H17NO3 | 343 | 342 [M − H] |
| 38 | 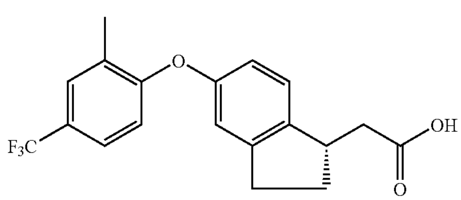 | C19H17F3O3 | 350 | 349 [M − H] |
| 39 | 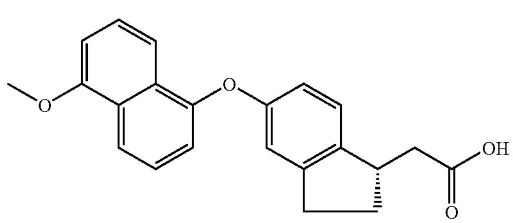 | C22H20O4 | 348 | 348 [M − H] |

TABLE 1-continued

| Example | Compound Structure | Molecular Fomula | MW (calc.) | MW Observed |
|---|---|---|---|---|
| 40 | 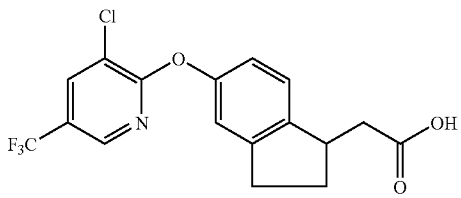 | C17H13ClF3NO3 | 371 | 370 [M − H] |
| 41 | 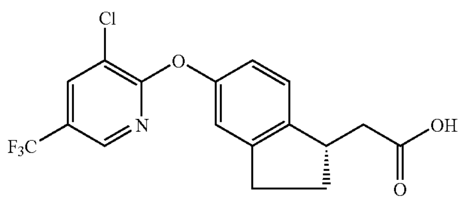 | C17H13ClF3NO3 | 371 | 370 [M − H] |
| 42 | 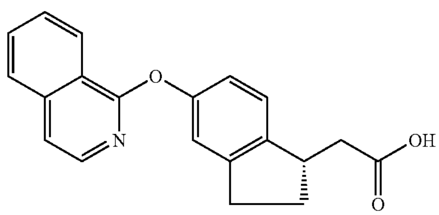 | C20H17NO3 | 319 | 318 [M − H] |
| 43 | 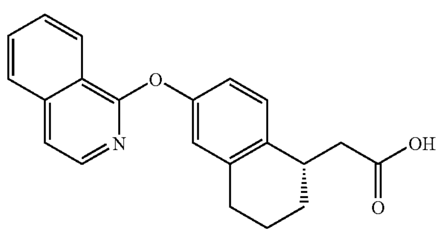 | C21H19NO3 | 333 | 332 [M − H] |
| 44 | 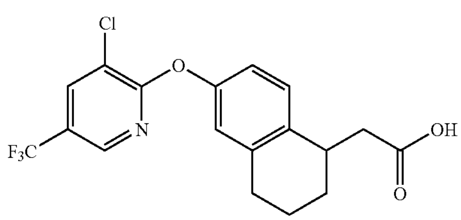 | C18H15ClF3NO3 | 385 | 384 [M − H] |
| 45 | 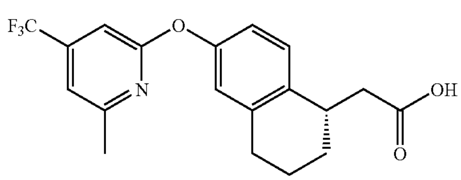 | C19H18F3NO3 | 365 | 364 [M − H] |
| 46 | 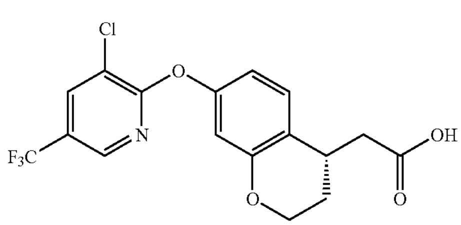 | C17H13ClF3NO4 | 387 | 386 [M − H] |

TABLE 1-continued

| Example | Compound Structure | Molecular Fomula | MW (calc.) | MW Observed |
|---|---|---|---|---|
| 47 | ![structure] | C22H18F3NO3 | 401 | 400 [M − H] |
| 48 | ![structure] | C21H16F3NO4 | 403 | 402 [M − H] |
| 48A | ![structure] | C17H12ClF3O4 | 372 | 371 [M − H] |

Example 49

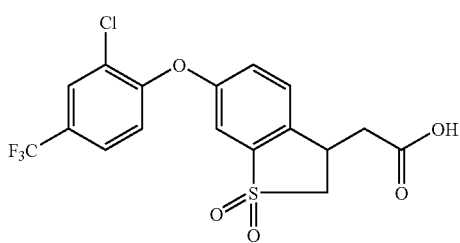

Step A

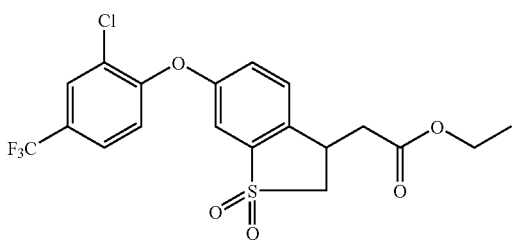

To a solution of material obtained from Step A of Example 1 (51 mg, 0.12 mmol) in dichloromethane (2 mL) was added meta-chloroperbenzoic acid (82 mg, 0.366 mmol). The mixture was stirred for 5 days at room temperature. The mixture was then diluted with dichloromethane, washed with an aqueous saturated NaHCO₃ solution and water, and dried with MgSO₄, filtered, and concentrated. The residue was purified by silica gel column chromatography using dichloromethane/methanol (30/1) as the eluant to afford the desired product. LCMS for C19H16ClF3O5S: calc. 448, observed 449 [M+H].

Step B

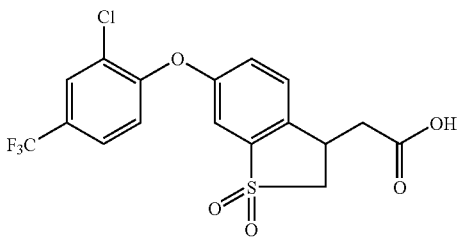

The material obtained from Step A was hydrolyzed to the desired acid following a procedure similar to the one described in Step B for the preparation of Example 1. LCMS for C17H12ClF3O5S: calc. 420, observed 421 [M+H].

Example 50

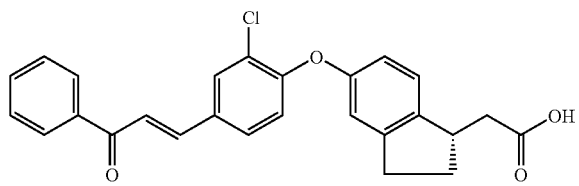

Example 20 (46 mg, 0.139 mmol) was dissolved in EtOH, followed by the addition of NaOMe (11.3 mg, 0.209 mmol). Acetophenone (16.7 mg, 0.139 mmol) was then added dropwise, and the reaction was stirred at room temperature for 4 hours. The reaction mixture was acidified with 1N HCl and the organic solvent was then removed in vacuo. The aqueous phase was extracted with ethyl acetate (2×), and the combined extracts were dried with anhydrous $Na_2SO_4$, filtered, and concentrated. The residue was purified by silica gel column chromatography using ethyl acetate/hexanes (1/1) as the eluant to afford the desired product. LCMS for C26H21ClO4: calc. 432, observed 431 [M−H].

Example 51

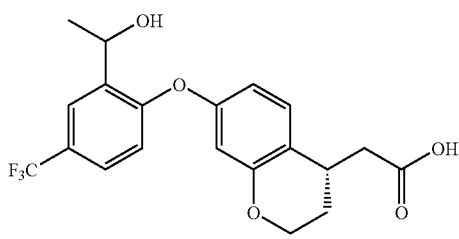

The compound was prepared from Example 21 and benzaldehyde following a procedure similar to the one described for Example 50. LCMS for C27H24O4: calc. 412, observed 411 [M−H].

Example 52

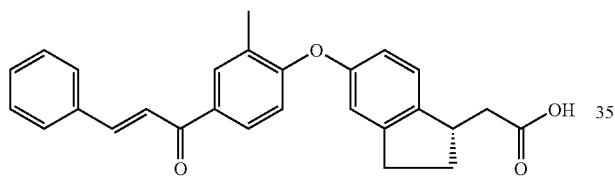

Example 31 (20 mg, 0.05 mmol) was dissolved in MeOH (1 mL) and the reaction mixture was cooled to 0° C. $NaBH_4$ (5.8 mg, 0.15 mmol) was slowly added. The reaction mixture was allowed to slowly warm to room temperature and stirred for another 2 hours. The reaction was quenched by addition of $H_2O$ followed by the removal of MeOH in vacuo. The aqueous phase was acidified with 1N HCl and extracted with ethyl acetate. The organic layer was dried with anhydrous $Na_2SO_4$, filtered, and concentrated to afford the desired compound. LCMS for C20H19F3O5: calc. 396, observed 395 [M−H].

Example 53

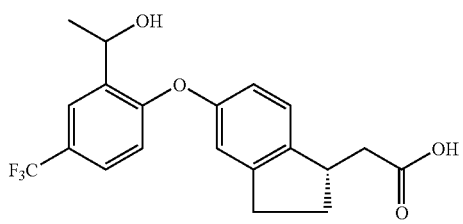

The compound was obtained from Example 33 following a procedure similar to the one described for preparation of Example 52. LCMS for C20H19F3O4: calc. 380, observed 379 [M−H].

Example 54

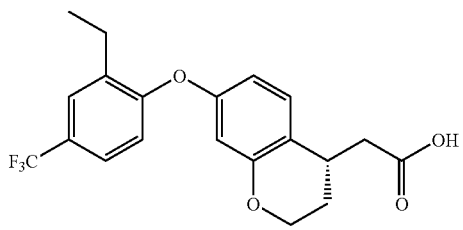

Example 52 (13 mg, 0.03 mmol) was mixed with TFA (0.2 mL) and triethylsilane (0.1 mL) in a capped tube, and the reaction mixture was heated at 75° C. for 1 hour in a microwave reactor. Volatiles were removed and the residue was purified by silica gel column chromatography using methanol/dichloromethane (10%) as the eluant to afford the desired product. LCMS for C20H19F3O4: calc. 380, observed 379 [M−H].

Example 54A

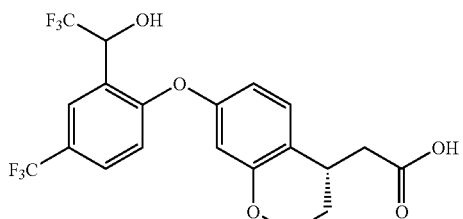

Example 32 (23 mg, 0.06 mmol) was mixed with a solution of trifluoromethyltrimethylsilane (0.18 mL, 0.5 M, 0.09 mmol), and the mixture was cooled to 0° C. A solution of tetrabutylammonium fluoride (0.18 mL, 1.0M in THF, 0.18 mmol) was gradually added to the mixture. The temperature was allowed to rise back to room temperature and the mixture was stirred for 1 hour at the same temperature. Excess 1N HCl was added, and the mixture was stirred for another 1 hour. Volatiles were removed in vacuo, and the residue was extracted with EtOAc. The organic extract was washed with brine, dried with MgSO₄, filtered, and concentrated. The residue was purified by preparative silica gel thin layer chromatography using dichloromethane/methanol (10/1) as the eluant to afford the desired product. LCMS for C20H16F6O5: calc. 450, observed 449 [M−H].

Example 54B

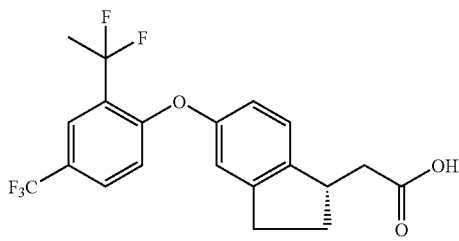

Step A

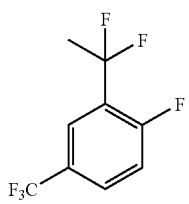

Into a sealed tube was added 4-fluoro-3-acetylbenzotrifluoride (500 mg, 2.43 mmol), Deoxofluor (1 mL) fluorinating agent, and a drop of HF-pyridine. After stirring at room temperature for 16 hours, an aqueous NaHCO₃ solution was added, and the mixture was extracted with dichloromethane (2×). The combined extracts were dried with MgSO₄, filtered and concentrated. The crude material was used in the next step without further purification.

Step B

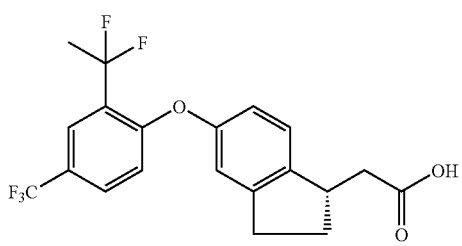

The compound was prepared following procedures similar to the one used in the preparation of Example 1, from Intermediate 1 and the aryl halide prepared in Step A. LCMS for C20H17F5O3: calc. 400, observed 399 [M−H].

Example 55

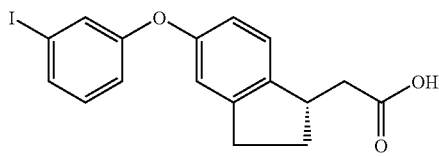

Step A

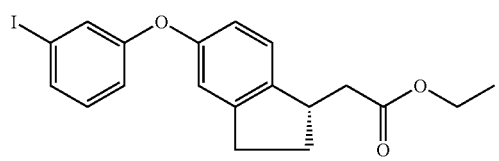

To a stirred solution of Intermediate 1 (1.9 g, 8.5 mmol) in dichloromethane (20 mL) was added 3-iodophenylboronic acid (3.0 g, 12.1 mmol), copper(II) acetate (2.0 g, 11 mmol), pyridine (3.2 mL, 40 mmol), and 4 Å molecular sieves (~2.5 g). The resulting mixture was stirred under an oxygen balloon at room temperature overnight. The reaction mixture was filtered, washed with dichloromethane, and concentrated. The greenish crude product was purified on a silica gel column, eluting with ethyl acetate (20-50%) in hexanes to afford the desired product. LCMS for C19H19IO3: calc. 422, observed 423 [M+H].

Step B

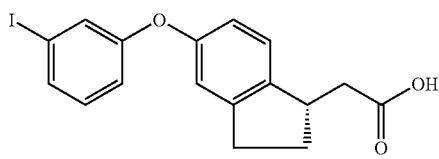

To a stirred solution of the above ethyl ester (45 mg, 0.1 mmol) in tetrahydrofuran (2 mL) was added 2N LiOH (0.5 mL, 1.0 mmol), followed by a few drops of methanol. After the completion of the hydrolysis (~3 hr, TLC), the reaction was quenched with aq. sat. ammonium chloride, and the crude product was purified by silica gel preparative TLC (10% methanol in dichloromethane, plus 0.5% acetic acid) to afford the desired product. LCMS for C17H15IO3: calc. 394, observed 395 [M+H].

Example 56

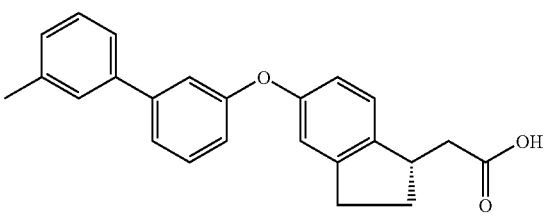

To a stirred solution of Example 55 (45 mg, 0.1 mmol) in tetrahydrofuran (2 ml) was added m-tolylboronic acid (15 mg, 0.1 mmol), followed by dppf (diphenylphosphinoferrocene, 10 mg, 0.01 mmol) and an aqueous solution of LiOH (0.5 mL, 2N, 1.0 mmol). The reaction tube was flushed with nitrogen, sealed, and stirred at 40° C. overnight. After cooling to room temperature, the reaction was quenched with aq. sat. ammonium chloride. The organic layer was loaded directly onto silica gel preparative TLC plates (1 mm), which were developed in 10% methanol in dichloromethane with ~0.5% acetic acid to afford the desired product. LCMS for C24H22O3: calc. 358, observed 359 [M+H].

Example 57

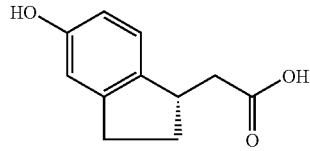

The compound was prepared from Example 55 following procedures similar to the one used in the preparation of Example 56. LCMS for C23H19FO3: calc. 362, observed 361 [M–H].

Example 58

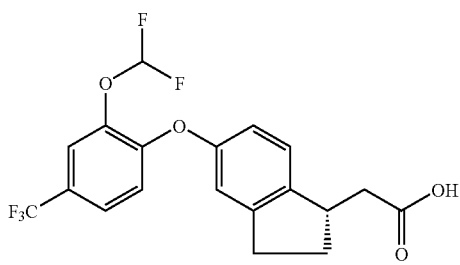

Step A

Sodium chlorodifluoroacetate (1.091 g, 6.94 mmol) and cesium carbonate (1.357 g, 4.16 mmol) were added to an N,N-dimethylformamide (5 mL) solution of 2-fluoro-5-trifluoromethyl phenol containing 10 volume % water (0.55 mL), and the reaction mixture was heated for 3 h at 100° C. After cooling to room temperature, the reaction mixture was diluted with ethyl acetate and washed with water (3×), brine (1 X). The organic layer was dried over sodium sulfate and concentrated to obtain the desired product (650 mg), which was used in the next step without further purification.

Step B

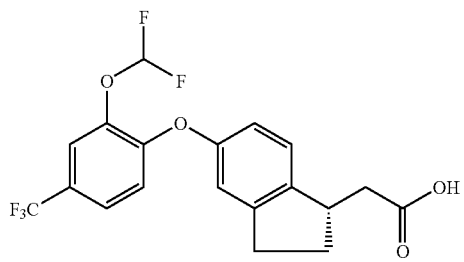

The compound was prepared from Intermediate 1 following a procedure similar to the one described in Step A of Intermediate 5a. LCMS for C11H12O3: calc. 192, observed 191 [M–H].

Step C

3-Difluoromethoxy-4-fluorobenzotrifluoride obtained in Step A (360 mg, 1.56 mmol) and cesium carbonate (1.02 g, 3.12 mmols) were mixed with the phenol obtained in Step B (200 mg, 1.04 mmol) in a sealed tube. Anhydrous DMF (5 mL) was then added, and the reaction mixture was degassed and flushed with nitrogen (2×), and was then heated at 120° C. for 3 h. The solvent was then removed and the reaction mixture was acidified with 2N HCl and extracted with ethyl acetate (3×). The combined organic layers were dried over sodium sulfate and concentrated to obtain the crude product, which was purified by silica gel column chromatography using methanol/dichloromethane (6%) as the eluant to afford the desired product. LCMS for C19H15F5O: calc. 402, observed 401 [M–H].

Example 59

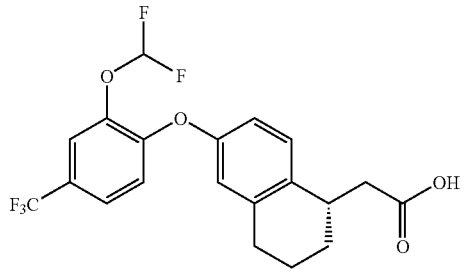

The compound was prepared from corresponding materials following a procedure similar to the one used in the preparation of Example 58. LCMS for C20H17F5O4: calc. 416, observed 415 [M–H].

Example 60

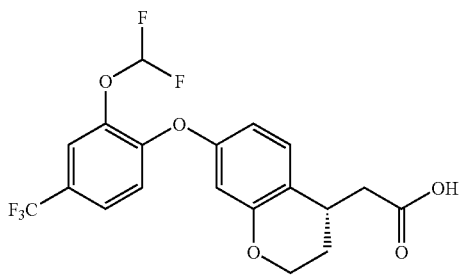

The compound was prepared from corresponding materials following a procedure similar to the one used in the preparation of Example 58. LCMS for C19H15F5O5: calc. 418, observed 417 [M–H].

Example 61

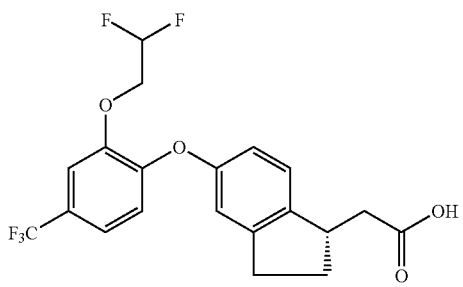

Step A

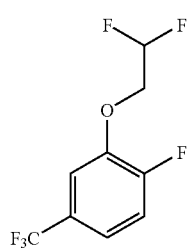

To a solution of 2-fluoro-5-trifluoromethyl phenol (100 mg, 0.55 mmol) in DMF (2 mL) was added 2-bromo-1,1-difluoroethane (121 mg, 1.11 mmol) and cesium carbonate (543 mg, 1.67 mmol). The reaction mixture was heated at 70° C. overnight before being diluted with ethyl acetate and washed with water. The organic layer was dried over sodium sulfate, filtered and concentrated to yield the crude product, which was used in the next step without further purification.

Step B

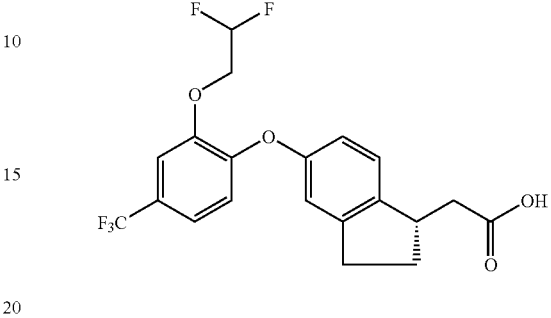

The compound was prepared from material obtained in Step A and the corresponding phenol obtained in Step B of Example 58, following a procedure similar to the one used in the preparation of Example 58. LCMS for C20H17F5O4: calc. 416, observed 415 [M–H].

Example 62

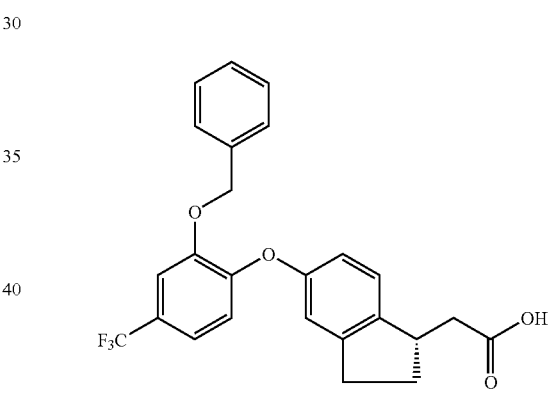

The compound was prepared from corresponding materials following a procedure similar to the one used in the preparation of Example 61. LCMS for C25H21F3O4: calc. 442, observed 441 [M–H].

Example 63

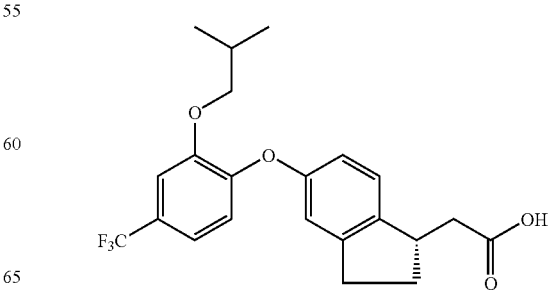

The compound was prepared from corresponding materials following a procedure similar to the one used in the preparation of Example 61. LCMS for C22H23F3O: calc. 408, observed 407 [M–H].

Example 64

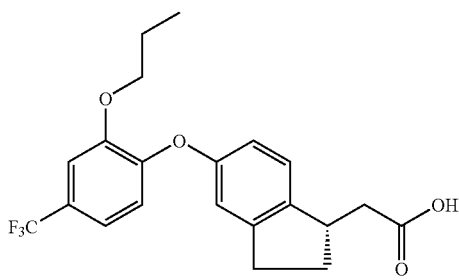

The compound was prepared from corresponding materials following a procedure similar to the one used in the preparation of Example 61. LCMS for C21H21F3O4: calc. 394, observed 393 [M–H].

Example 65

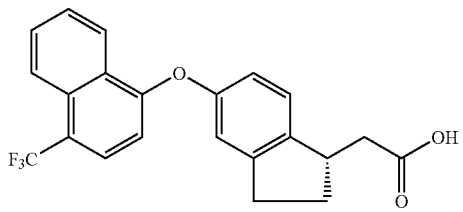

Step A

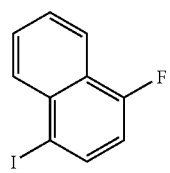

1-Bromo-4-fluoronaphthalene (1.3 g, 5.78 mmol), CuI (275 mg, 1.44 mmol), rac-trans-N,N'-dimethylcyclohexane-1,2-diamine (424 mg, 2.89 mmol), and NaI (2.16 g, 14.4 mmol) were added to a sealed tube, degassed, and dioxane (10 mL) was then added. The reaction mixture was again degassed and flushed with nitrogen and heated at 110° C. for 24 hours. The reaction mixture was cooled to room temperature, diluted with ethyl acetate, and the solid was filtered off. The filtrate was concentrated to obtain the crude product, which was purified by silica gel column chromatography (10% ethyl acetate/hexane as the eluant) to obtain the desired compound.

Step B

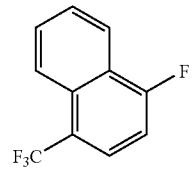

1-Iodo-4-fluoronaphthalene obtained from Step A (2.89 g, 10.640 mmol), CuI (5.07 g, 26.5 mmol), methyl (fluorosulfonyl)difluoroacetate (13.5 mL, 106.4 mmol), and diisopropyl ethyl amine (18.5 mL, 106.4 mmol) were added to a sealed tube and degassed, and DMF (10 mL) was then added. The reaction mixture was then degassed, flushed with nitrogen, and heated at 75° C. for 12 hours. The reaction mixture was then washed with water and extracted with ethyl acetate (3×). The combined organic layers were washed with water and sodium bicarbonate, dried over sodium sulfate, and concentrated to obtain the crude product, which was purified by column chromatography (10% ethyl acetate/hexanes as the eluant) to obtain the desired compound.

Step C

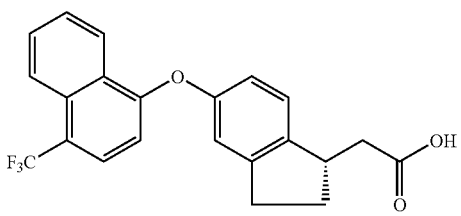

The compound was prepared from material obtained in Step B and the corresponding phenol obtained in Step B of Example 58, following a procedure similar to the one used in the preparation of Example 58. LCMS for C22H17F3O3: calc. 386, observed 385 [M–H].

Example 66

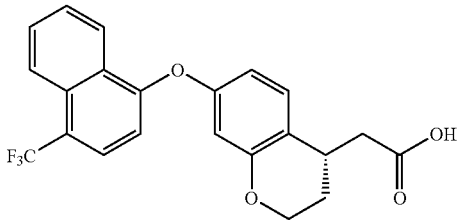

The compound was prepared from corresponding materials following a procedure similar to the one used in the preparation of Example 65. LCMS for C22H17F3O4: calc. 402, observed 403 [M–H].

Example 67

Step A

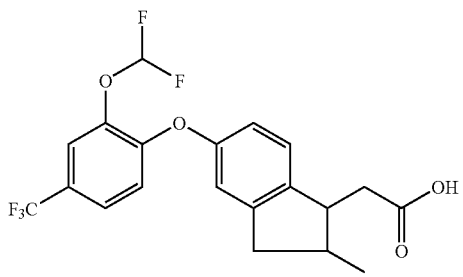

Triethyl phosphonoacetate (0.85 mL, 4.26 mmol) was added dropwise to a solution of sodium hydride (148 mg, 3.69 mmol) in anhydrous THF (10 mL) at 0° C. The mixture was stirred at 0° C. for 15 minutes, and to this mixture was added 2-methyl-5-methoxy indanone (500 mg, 2.84 mmol). The reaction mixture was gradually warmed to room temperature and stirred overnight at room temperature under nitrogen. The reaction mixture was then refluxed at 70° C. for 30 hours. It was then quenched with aqueous NH$_4$Cl and extracted with ethyl acetate (3×). The combined organic layers were dried over sodium sulfate, filtered and concentrated. The residue was purified by silica gel column chromatography (0-10% ethyl acetate/hexanes as the eluant). LCMS for C15H18O3: calc. 246, observed 247 [M+H].

Step B

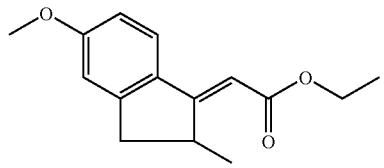

The material obtained from Step A (310 mg, 1.26 mmol) was dissolved in methanol (10 mL), and palladium on carbon (300 mg, 10 weight %) was added to the solution. The solution was stirred under hydrogen (balloon) for 2 hours. The catalyst was filtered off and the filtrate concentrated to afford the product. LCMS for C15H20O3: calc. 248, observed 249 [M+H].

Step C

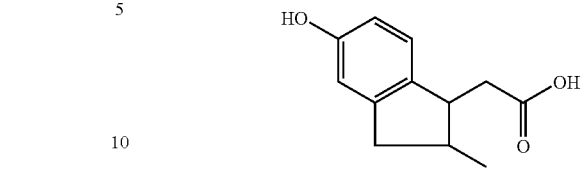

The material obtained from Step B (266 mg, 1.07 mmol) was dissolved in anhydrous dichloromethane (DCM) (5 mL) and cooled to 0° C. A BBr$_3$ solution (1M in DCM, 2.14 mL, 2.14 mmol) was then added and the reaction mixture was warmed from 0° C. to room temperature and stirred at room temperature for 3 hours. The reaction mixture was poured into ice-water and extracted with ethyl acetate (3×). The combined organic layers were dried over sodium sulfate and filtered to afford the crude acid, which was used in the next step without further purification.

Step D

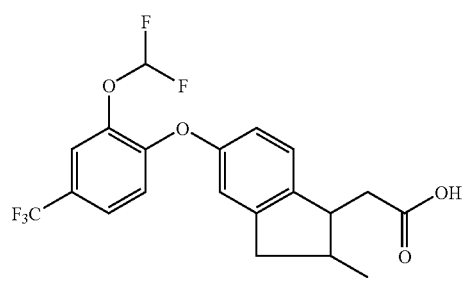

The compound was prepared from the material obtained from Step C following a procedure similar to the one used in the preparation of Example 58. LCMS for C20H17F5O4: calc. 416, observed 415 [M–H].

Example 68

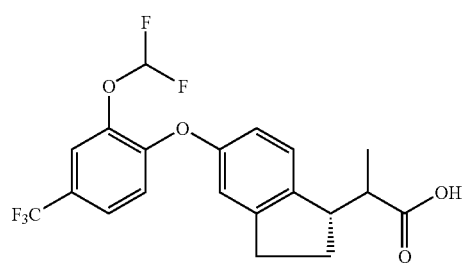

Step A

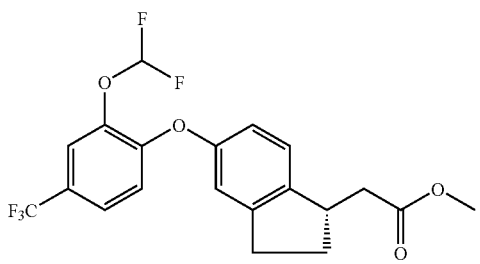

Example 58 (219 mg, 0.54 mmol) was dissolved in anhydrous methanol (5 mL), and a catalytic amount of 4.0M HCl in dioxane was then added, and the reaction mixture was heated in a capped tube for 1 hour. The crude methyl ester was obtained by removing the solvents and was purified by silica gel column chromatography (20% ethyl acetate/hexane as the eluant). LCMS for C20H17F5O: calc. 416, observed 417 [M+H].

Step B

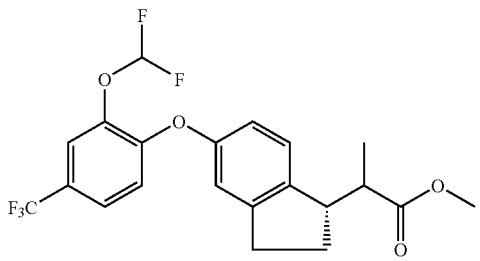

The material obtained from Step A (65 mg, 0.16 mmol) was azeotroped in toluene, dissolved in anhydrous THF (2 mL) and cooled to −78° C. Sodium bis-trimethylsilylamide (0.2 mL, 0.188 mmol) was then added and the reaction mixture was stirred at −78° C. for 5 minutes, warmed to 0° C., and methyl iodide (14.6 μL, 0.234 mmol) was added. The reaction mixture was slowly warmed to room temperature and stirred at room temperature for 1 hour. The reaction mixture was quenched by addition of aqueous NH4Cl and extracted with ethyl acetate (3×). The combined organic layers were dried over sodium sulfate, filtered, and concentrated to give the crude product, which was purified by silica gel chromatography (10% ethyl acetate/hexanes as the eluant). 1H NMR of the material obtained showed a mixture of two isomers (ca 1:5). LCMS for C21H19F5O: calc. 430, observed 431 [M+H].

Step C

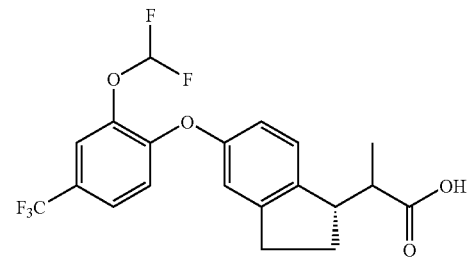

The material obtained from Step B (12 mg, 0.0279 mmol) was dissolved in ethanol (1 mL), and 5 N NaOH solution (0.03 mL, 0.14 mmol) was added. The reaction mixture was then heated in a capped tube at 80° C. for 2 hours. The reaction mixture was acidified using 2N HCl and extracted with ethyl acetate (3×). The combined organic layers were dried over sodium sulfate and concentrated to afford the crude product, which was then purified by silica gel preparative thin layer chromatography (6% methanol in dichloromethane) to afford the desired compound as a mixture of two isomers (ca 1:5 by 1H NMR). LCMS for C20H17F5O: calc. 416, observed 415 [M−H].

Example 69

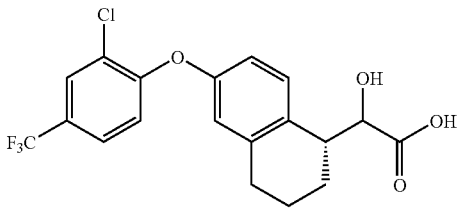

Step A

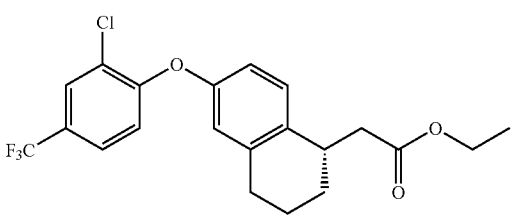

The material was obtained from corresponding materials following a procedure similar to the one described in Step A in Example 1. LCMS for C21H20ClF3O3: calc. 412, observed 413 [M+H].

Step B

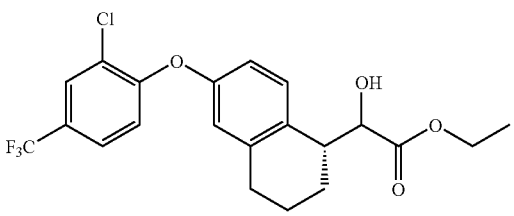

To the material obtained in Step A (1.9 g, 5.85 mmol) in dry THF (30 mL) was added sodium hexamethyldisilazide (NaH-MDS) (6.43 mL, 1M solution, 6.4 mmol) at −78° C. After 30 minutes, trimethylchlorosilane (TMSCl) (6.4 mL, 1M solution in THF, 6.43 mmol) was added. The reaction was allowed to warm to room temperature slowly overnight. THF was then removed in vacuo and the residue was suspended in hexane. This hexane suspension was filtered. This filtrate was added slowly to a suspension of meta-chloroperbenzoic acid (mCPBA) (1.31 g, 77% max, 5.85 mmol) in hexane (30 mL). After addition, the mixture was stirred at room temperature for another 1 hour before CH2Cl2 (50 mL) was added. To this clear solution was then added tetra-n-butylammonium fluoride (TBAF) (1M THF solution, 15 mL). After 1 hour, the reaction was concentrated and purified on a silica gel column (20% EtOAc/hexane) to give the desired product as light yellow oil. LC-MS for C21H20ClF3O4: calc 428, found 451 [M+Na+]

Step C

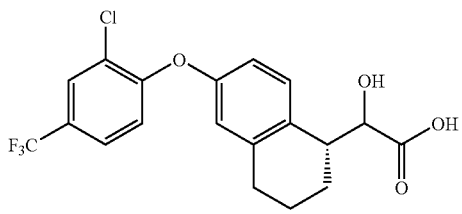

To the product obtained in Step B (20 mg) in THF (3 mL), MeOH (2 mL) and water (0.5 mL) was added LiOH monohydrate (5 mg). The reaction was stirred at room temperature for 2 hours before quenching with AcOH (0.2 mL). The mixture was concentrated, and the residue was purified by reverse phase HPLC (YMC-Pack Pro C18 5 micron, 20% to 80% $CH_3CN/H_2O$ with 0.1% TFA) to afford the desired product. LC-MS for $C19H16ClF3O4$: calc 400, found 401 $[M+H^+]$.

Example 70

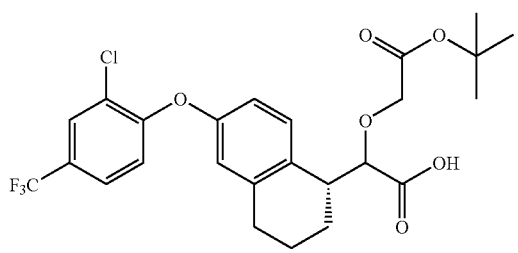

Step A

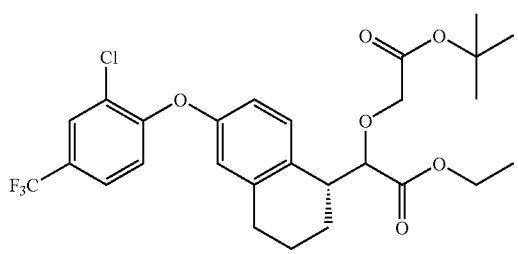

To the product from Step B in Example 69 (176 mg, 0.411 mmol) in THF (2 mL) was added NaHMDS (1 M THF solution, 0.411 mL) at −20° C. followed by t-butylbromoacetate (0.616 mmol, 0.091 mL). The reaction was stirred for another 20 minutes at −20° C. before quenching with saturated $NH_4Cl$ aqueous solution (20 mL). The mixture was extracted with EtOAc (3×15 mL). The combined organic layers were washed with water (20 mL), brine (20 mL), dried over anhydrous $Na_2SO_4$, filtered and concentrated to give the product, which was used in the next step without further purification.

Step B

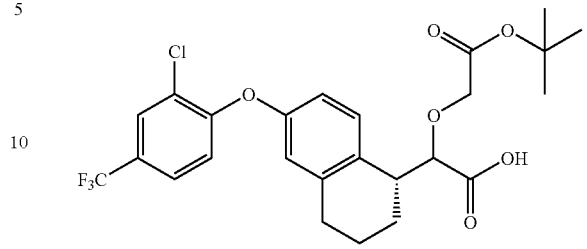

To the crude product from Step A (half of the material, ~0.2 mmol) was added THF (12 mL), MeOH (8 mL) and water (2 mL) followed by LiOH monohydrate (25 mg). The reaction was stirred at room temperature for 2 hours and then quenched with AcOH (0.5 mL). The mixture was concentrated to an oil and then purified by reverse phase HPLC (YMC-Pack Pro C18 5 micron, 20% to 80% $CH_3CN/H_2O$ with 0.1% TFA) to give the desired product. LC-MS for $C25H26ClF3O6$: calc 514, found 457 $[M-^tBu]$.

Example 71

A solution of Example 70 (10 mg) in 30% TFA in $CH_2C_{12}$ (5 mL) was stirred at room temperature for 1 hour. The reaction was then concentrated in vacuo and the residue was purified by reverse phase HPLC (YMC-Pack Pro C18 5 micron, 20% to 80% $CH_3CN/H_2O$ with 0.1% TFA) to give the desired compound. LC-MS for $C21H18ClF3O6$: calc 458, found 457 $[M-H]$.

Examples 72A and 72B

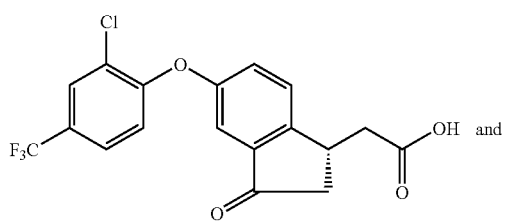

and

-continued

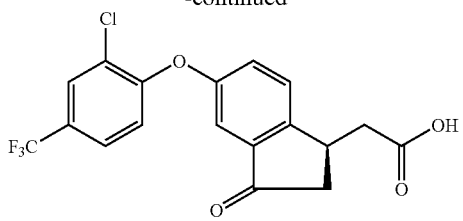

Step A

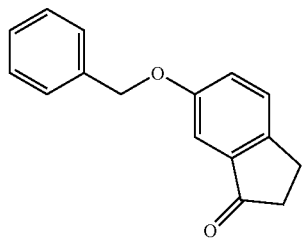

A solution of 6-(hydroxy)indane-1-one (5.0 g, 34 mmol) in 35 mL of DMF was treated with sodium hydride (60% suspension in mineral oil, 1.62 g, 40 mmol) at 0° C. After stirring 30 min. at room temperature, benzyl bromide (4.8 mL, 40 mmol) was added slowly, and the solution was stirred 12 h. After quenching with saturated ammonium chloride, the mixture was extracted with ethyl acetate. The combined organic layers were washed with brine, dried over sodium sulfate, filtered and concentrated. The resulting solid was recrystallized from ethyl acetate/hexane to provide the product. LC-MS for C16H14O2: calc 238, found 239 [M+H].

Step B

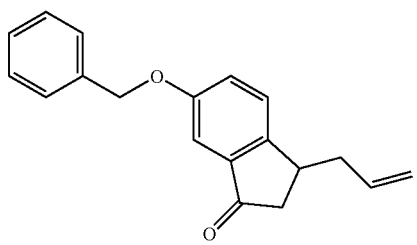

To a solution of diisopropylamine (2.94 mL, 21 mmol) in 14 mL of THF at −78° C. was added dropwise n-butyllithium (1.6 M in hexane, 12.1 mL, 19 mmol). After 30 min. at −78° C., a solution of 6-(benzyloxy)indan-1-one (2.0 g, 8.4 mmol) in 14 mL THF was added via canula. The solution was stirred 1 h at −78° C., then warmed slowly to room temperature over 4 h. The solution was cooled to −20° C., treated with allyl bromide (1.22 g, 10 mmol), and allowed to warm to 0° C. over 1 h. The reaction was quenched with saturated ammonium chloride and extracted with ethyl acetate. The combined organic layers were washed with brine, dried over sodium sulfate, filtered, and concentrated. Purification was carried out by silica gel column chromatography, eluting with ethyl acetate (2-20%) in hexane, to provide the desired product. LC-MS for C19H18O2: calc 278, found 279 [M+H].

Step C

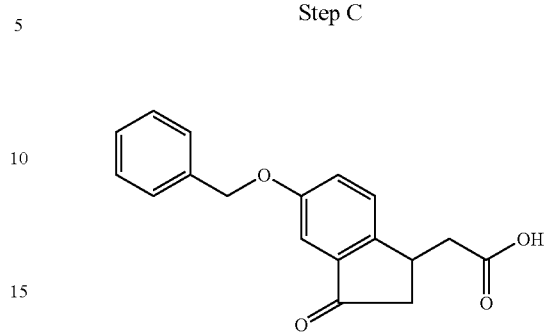

A solution of KMnO4 (2.59 g, 16.4 mmole) in water (180 ml) was added dropwise to a rapidly stirring mix of 3-allyl-6-(benzyloxy)indan-1-one and NaIO4 (4.49 g, 21 mmole) in acetone (60 ml) and acetic acid (60 ml) at room temp. A reddish-brown precipitate (MnO2) formed. After 1.5 h, additional NaIO4 (1.3 eq, 13.6 mmole, 2.8 g) was added, followed after 1.5 h by a final addition of NaIO4 (0.5 eq, 5.3 mmole, 1.13 g), and the mix was stirred at rt for 18 h. Ethylene glycol (43 ml) was added, and the mix was stirred at room temp for 1 hour. The mix was filtered through a plug of celite plus a layer of silica gel. The filter cake was washed with 10% MeOH/CH2Cl2 (750 ml), the filtrate was transferred to a separatory funnel, and the layers were separated. The aqueous phase was brought to pH 2 and extracted 3× with EtOAc. All organic phases were combined, dried (MgSO4), and concentrated to a thick oil. The oil was dissolved in EtOAc and extracted 2× with saturated NaHCO3. The combined aqueous extracts were brought to pH 2 and extracted 3× with EtOAc. The combined extracts were dried (MgSO4), concentrated and azeotroped from toluene to give the desired product. The original EtOAc solution containing the thick oil was resubjected to further extractions with NaHCO3, acidification, extraction, drying and concentration to give additional [5-(benzyloxy)-3-oxo-2,3-dihydro-1H-inden-1-yl]acetic acid. LC-MS for C18H16O4: calc 296, found 297 [M+H].

Step D

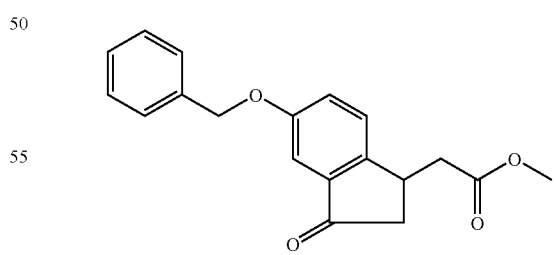

A solution of TMS-diazomethane (2.0M/hexane) was added dropwise to a solution of [5-(benzyloxy)-3-oxo-2,3-dihydro-1H-inden-1-yl]acetic acid (1.4 g, 4.72 mmol) in methylene chloride (25 ml) and methanol (15 ml) until the yellow color persisted. This required more than 3 ml. After stirring for 15 min the reaction was concentrated to give crude product. The crude product was chromatographed on a silica gel column in a 5-40% EtOAc/Hex gradient to afford the desired product. LC-MS for C19H18O4: calc 310, found 311 [M+H].

Step E

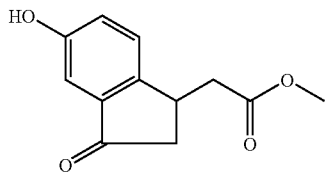

To a solution of methyl [5-(benzyloxy)-3-oxo-2,3-dihydro-1H-inden-1-yl]acetate (1.0 g, 3.22 mmol) and 1-methyl-cyclohexa-1,4-diene (10 ml, 89 mmol) in ethanol (30 ml) was added 10% Pd/C (0.686 g, 0.644 mmol), and the mix was stirred at 55° C. After 1 hour the mix was filtered through a bed of Celite, washing with ethanol The filtrate was concentrated and the residue was concentrated from ether-hexane to give methyl (5-hydroxy-3-oxo-2,3-dihydro-1H-inden-1-yl) acetate. LC-MS for C12H12O4: calc 220, found 221 [M+H].

Step F

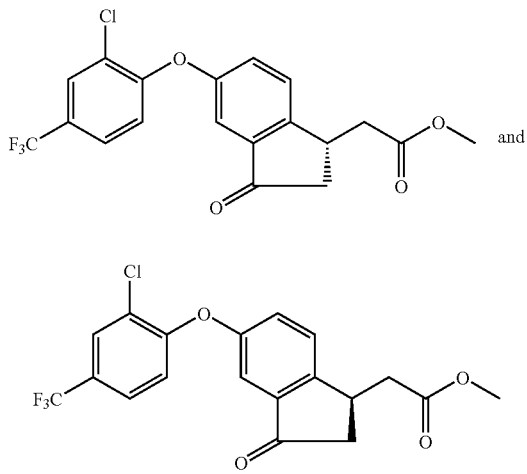

Cesium carbonate was added to a solution of methyl (5-hydroxy-3-oxo-2,3-dihydro-1H-inden-1-yl)acetate and 2-chloro-1-fluoro-4-(trifluoromethyl)benzene in DMF (3 ml), and the mix was stirred at 80° C. for 3 hours. The reaction was diluted with EtOAc and washed with 1N HCl, water (2×), brine, dried (MgSO₄), and concentrated. The crude product was chromatographed on a silica gel column in a 5-40% EtOAc/Hex gradient and was further purified by silica gel preparative thin layer chromatography (7:3 Hex/EtOAc). The enantiomers were separated on a ChiralPak 2 cm×23 mm IA column eluting with 10% EtOH/Heptane. LC-MS for C19H14ClF3O4: calc 398, found 399 [M+H].

Step G

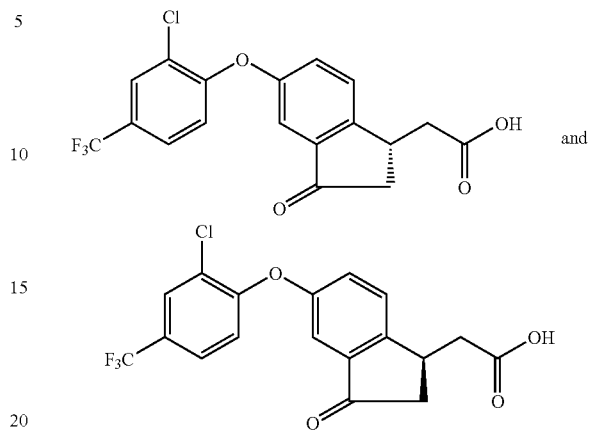

A solution of lithium hydroxide (1 M, 0.188 ml) was added to solutions of 25 mg of each of the two isomers of 5-[2-chloro-4-(trifluoromethyl)phenoxy]-3-oxo-2,3-dihydro-1H-inden-1-yl}acetate in methanol (1 ml), and each mixture was stirred at room temperature. After completion of the reaction (5-9 hours), the mixtures were concentrated (cold), and the residues were dissolved in water, brought to pH1, and extracted 3× with ethyl acetate. The combined extracts for each of the two products were dried (MgSO₄) and concentrated to give the desired acids. LC-MS for C18H12ClF3O4: calc 384, found 385 [M+H].

Example 73

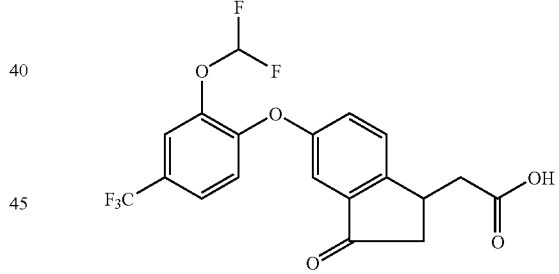

Example 73 was obtained from corresponding materials following a procedure similar to the one described for Examples 72A and 72B. LC-MS for C19H13F5O5: calc 416, found 417 [M+H].

Example 74

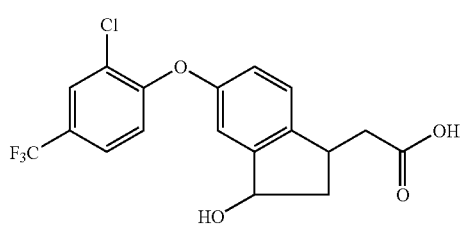

Step A

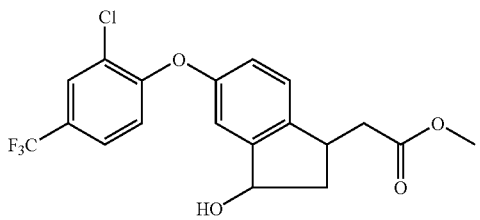

The compound was obtained from the material obtained in Step F of Example 72A and 72 B (before chiral separation), following a procedure similar to the one described in Example 52. LC-MS for C19H16ClF3O4: calc 400, found 401 [M+H].

Step B

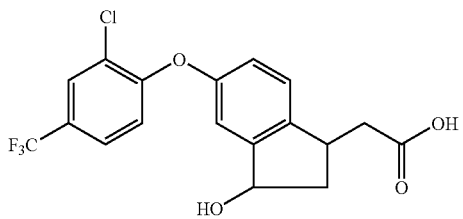

The compound was prepared from the material obtained in Step A, following a procedure similar to the one described in Step G for Example 72A and 72B. LC-MS for C18H14ClF3O4: calc 386, found 385 [M−H].

Example 75

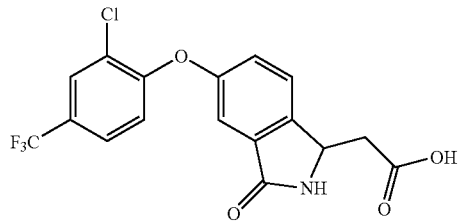

Step A

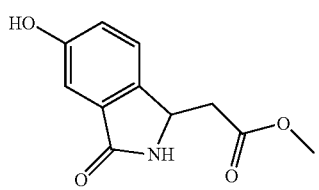

To a stirred solution of (5-hydroxy-3-oxo-2,3-dihydro-1H-isoindol-1-yl)acetic acid (0.45 g, 2.2 mmol) in 10 ml of methanol at 0° C. was added thionyl chloride (0.16 mL, 2.4 mmol). The reaction mixture was warmed to room temperature, and after stirring 2 h was concentrated. The crude product was purified by silica gel chromatography, eluting with ethyl acetate (10-100%) in hexane. LC-MS for C11H11NO4: calc 221, found 222 [M+H].

Step B

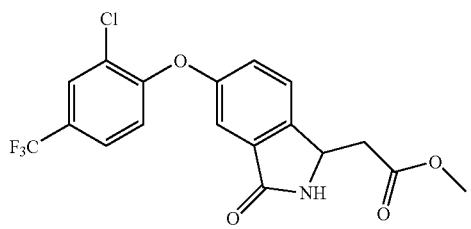

To a stirred solution of methyl (5-hydroxy-3-oxo-2,3-dihydro-1H-isoindol-1-yl)acetate (0.33 g, 1.6 mmol) in 5 ml of DMF was added 3-chloro-4-fluorobenzotrifluoride (0.40 g, 2.0 mmol) and cesium carbonate (0.782 g, 2.4 mmol). The reaction mixture was heated at 80° C. for 12 h. After cooling to room temperature, the reaction mixture was diluted with ethyl acetate and saturated sodium bicarbonate. The aqueous layer was extracted with ethyl acetate. The combined organic layers were washed with water (2×) and brine, dried over sodium sulfate, filtered and concentrated. The crude product was purified by silica gel chromatography, eluting with ethyl acetate (5-30%) in hexane. LC-MS for C18H13ClF3NO4: calc 399, found 400 [M+H].

Step C

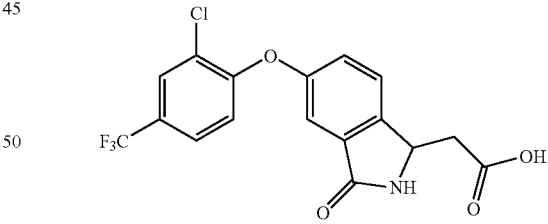

To a stirred solution of methyl {5-[2-chloro-4-(trifluoromethyl)phenoxy]-3-oxo-2,3-dihydro-1H-isoindol-1-yl}acetate (20 mg, 0.050 mmol) in MeOH (0.5 mL) was added 1 N LiOH (0.5 mL) at 0° C. The reaction mixture was stirred for 4 hours, warming to room temperature, then concentrated, and diluted with water and ethyl acetate. The organic layer was discarded, and the aqueous layer was adjusted to pH~2 with 0.5 N HCl, and then was extracted with ethyl acetate. The combined organic layers were washed with brine, dried over sodium sulfate, filtered and concentrated to afford the desired product. LC-MS for C17H11ClF3NO4: calc 385, found 384 [M−H].

Example 76

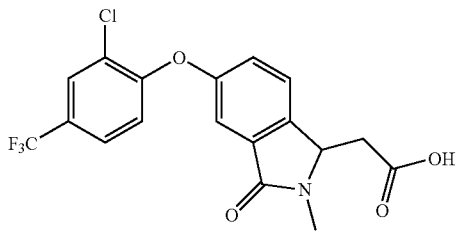

Step A

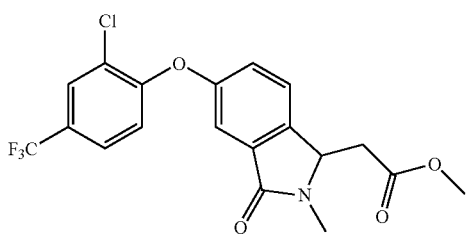

To a stirred solution of methyl {5-[2-chloro-4-(trifluoromethyl)phenoxy]-3-oxo-2,3-dihydro-1H-isoindol-1-yl}acetate obtained in Step B of Example 75 (26 mg, 0.065 mmol) in 1 mL of DMF at 0° C. was added sodium hydride (60% suspension in mineral oil, 3.5 mg, 0.087 mmol). After warming to room temperature and stirring 30 min, the reaction mixture was treated with methyl iodide (0.005 mL, 0.078 mmol) at 0° C. The reaction mixture was warmed slowly to room temperature and stirred 12 h. The reaction mixture was quenched with saturated ammonium chloride and diluted with ethyl acetate. The aqueous layer was extracted with ethyl acetate. The combined organic layers were washed with water (2x) and brine, dried over sodium sulfate, filtered and concentrated. The crude product was purified by silica gel chromatography, eluting with ethyl acetate (10-80%) in hexane. LC-MS for C19H15ClF3NO4: calc 413, found 414 [M+H].

Step B

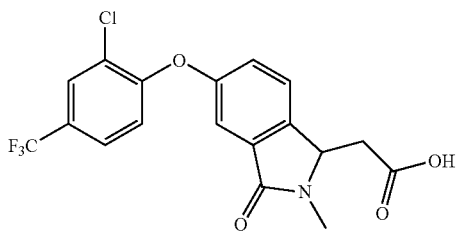

To a stirred solution of methyl {5-[2-chloro-4-(trifluoromethyl)phenoxy]-2-methyl-3-oxo-2,3-dihydro-1H-isoindol-1-yl}acetate (26 mg, 0.063 mmol) in MeOH (0.5 mL) was added 1 N LiOH (0.5 mL) at 0° C. The reaction mixture was stirred for 2 hours, warming to room temperature, then concentrated, and diluted with water and ethyl acetate. The organic layer was discarded and the aqueous layer was adjusted to pH~2 with 0.5 N HCl, then extracted with ethyl acetate. The combined organic layers were washed with brine, dried over sodium sulfate, filtered and concentrated to afford the product. LC-MS for C18H13ClF3NO4: calc 399, found 398 [M–H].

Example 77

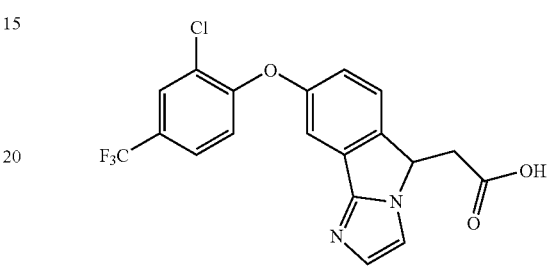

To a stirred solution of methyl {5-[2-chloro-4-(trifluoromethyl)phenoxy]-3-oxo-2,3-dihydro-1H-isoindol-1-yl}acetate obtained in Step B of Example 75 (30 mg, 0.075 mmol) in methylene chloride (0.5 mL) at 0° C. was added Meerwein's salt (13 mg, 0.090 mmol). After stirring 12 h at room temperature, the reaction mixture was diluted with water and extracted with ethyl acetate. The combined organic layers were washed with brine, dried over sodium sulfate, filtered and concentrated. The resulting residue was dissolved in 1 mL of acetonitrile, treated with aminoacetaldehyde diethyl acetal (10 mg, 0.075 mmol) and heated at reflux for 4 h. The reaction mixture was cooled to room temperature, treated with concentrated hydrochloric acid (0.5 mL) and heated at reflux for 1 h, after which it was cooled to room temperature and concentrated. The resulting residue was diluted with water and ethyl acetate, the initial organic layer was discarded, and the aqueous layer was adjusted to pH~2 with 0.5 N HCl and extracted with ethyl acetate. The combined organic layers were washed with brine, dried over sodium sulfate, filtered, and concentrated. Purification by reverse phase HPLC (0.1% TFA/H2O/acetonitrile gradient) provided the desired product. LC-MS for C19H12ClF3N2O3: calc 408, found 409 [M+H].

Example 78

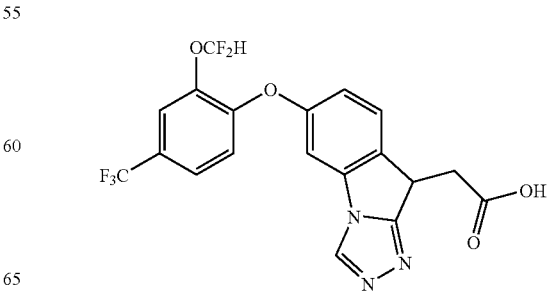

Step A

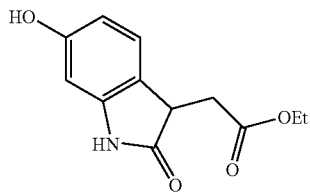

To a solution of (6-methoxy-2-oxo-2,3-dihydro-1H-indol-3-yl)acetic acid (0.221 g, 1.0 mmol) in 5 mL ethanol at 0° C. was added thionyl chloride (0.35 g, 3.0 mmol) dropwise. After stirring 2 h at room temperature, the reaction mixture was concentrated. The residue was dissolved in methylene chloride, washed with saturated sodium carbonate, dried over sodium sulfate, and concentrated. Silica gel chromatography, eluting with ethyl acetate (10-100%) in hexane, provided the intermediate ester, which was dissolved in methylene chloride and treated with boron tribromide (1.0 M in methylene chloride, 3.0 mL) at 0° C. The reaction was warmed to room temperature and stirred 12 h. After quenching with saturated sodium carbonate, the reaction mixture was transferred to a separatory funnel, and the aqueous layer extracted with ethyl acetate. The combined organic layers were washed with brine, dried over sodium sulfate, and concentrated to afford the product. LC-MS for C12H13NO4: calc 235, found 236 [M+H].

Step B

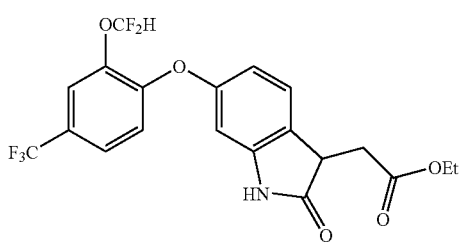

To a stirred solution of ethyl (6-hydroxy-2-oxo-2,3-dihydro-1H-indol-3-yl)acetate (0.0.61 g, 0.26 mmol) in 1.5 ml of DMF was added 3-(difluoromethoxy)-4-fluorobenzotrifluoride (0.065 g, 0.28 mmol) and cesium carbonate (0.129 g, 0.38 mmol). The reaction mixture was heated at 80° C. for 12 h. After cooling to room temperature, the reaction mixture was diluted with ethyl acetate and saturated sodium bicarbonate. The aqueous layer was extracted with ethyl acetate. The combined organic layers were washed with water (2×) and brine, dried over sodium sulfate, filtered and concentrated. The crude product was purified by silica gel chromatography, eluting with ethyl acetate (8-100%) in hexane. LC-MS for C20H16F5NO5: calc 445, found 446 [M+H].

Step C

To a solution of ethyl {6-[2-(difluoromethoxy)-4-(trifluoromethyl)phenoxy]-2-oxo-2,3-dihydro-1H-indol-3-yl}acetate (65 mg, 0.274 mmol) in 1.5 mL methylene chloride at 0° C. was added Meerwein's salt (41 mg, 0.090 mmol). After stirring 12 h at room temperature, the reaction mixture was diluted with water and extracted with ethyl acetate. The combined organic layers were washed with brine, dried over sodium sulfate, filtered, and concentrated. The resulting residue was dissolved in 2 mL of acetonitrile, treated with formyl hydrazine (10 mg, 0.164 mmol), and heated at reflux for 12 h. The reaction mixture was cooled to room temperature and concentrated. Purification by reverse phase HPLC (0.1% TFA/H2O/acetonitrile gradient) provided the desired product. LC-MS for C21H16F5N3O4: calc 469, found 470 [M+H].

Step D

To a stirred solution of ethyl {6-[2-(difluoromethoxy)-4-(trifluoromethyl)phenoxy]-9H-[1,2,4]triazolo[4,3-a]indol-9-yl}acetate (26 mg, 0.063 mmol) in MeOH (0.5 mL) and THF (0.5 mL) was added 1 N LiOH (0.5 mL) at 0° C. The reaction mixture was stirred for 2 hours, and then was concentrated and diluted with water and ethyl acetate. The organic layer was discarded, the aqueous layer was adjusted to pH~2 with 0.5 N HCl, and then was extracted with ethyl acetate. The combined organic layers were washed with brine, dried over sodium sulfate, filtered and concentrated to afford the product. LC-MS for C19H12F5N3O4: calc 441, found 442 [M+H].

Example 79

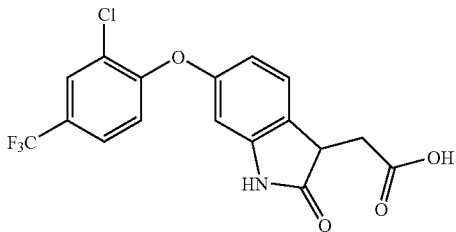

Step A

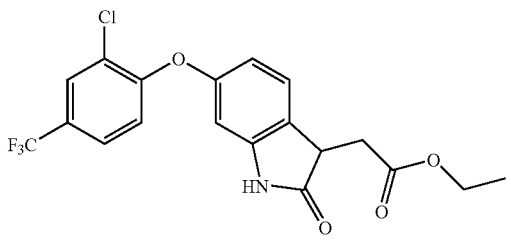

Compound was prepared from the material obtained from Step A of Example 78 and 3-chloro-4-fluorobenzotrifluoride, following a procedure similar to the one described for Step B of Example 78. LC-MS for C19H15ClF3NO4: calc 413, found 414 [M+H].

Step B

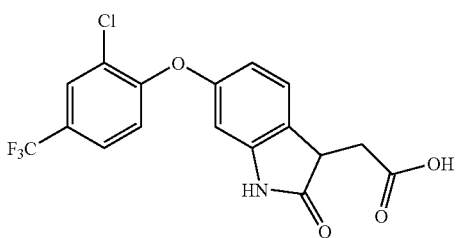

Compound was prepared from the material obtained in Step A, following a procedure similar to the one described in Step D of Example 78. LC-MS for C17H11ClF3NO4: calc 385, found 386 [M+H].

What is claimed is:
1. A compound of formula I, or a pharmaceutically acceptable salt thereof:

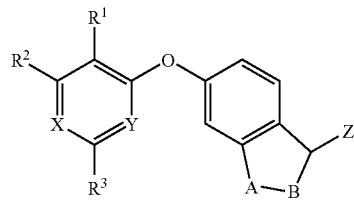

I wherein A is selected from the group consisting of —CH$_2$—, —CF$_2$—, —O—, —N(R$^6$)—, —S—, —S(O)—, —S(O)$_2$—, —C(=O)—, and —CH(OH)—;

B is selected from the group consisting of —CH$_2$—, —CH$_2$CH$_2$—, and —CH(CH$_3$)—;
or alternatively -A-B- is selected from the group consisting of —N(R$^6$)C(=O)— and —C(=O)N(R$^6$)—, or -A-B- represents two atoms that are connected to form one side of a 5-membered heteroaromatic ring having 1-3 heteroatoms independently selected from O, N and S, where the 5-membered heteroaromatic ring is optionally substituted with 1-3 groups independently selected from halogen, CH$_3$, CF$_3$, —OCH$_3$, and —OCF$_3$;
X is selected from =C(R$^4$)— and =N—; and Y is selected from =C(R$^5$)— and =N—; with the proviso that X and Y are not both =N—;
Z is —CR$^7$R$^8$CO$_2$R$^9$;
Heterocycle is a 5-6 membered saturated or partly saturated monocyclic heterocyclic ring having 1-3 heteroatoms independently selected from O, N and S;
Heteroaryl is a 5-6 membered monocyclic heteroaromatic ring having 1-3 heteroatoms independently selected from O, N and S;
R$^1$, R$^2$, R$^3$, R$^4$, and R$^5$ are each independently selected from the group consisting of H, halogen, —CN, —NO$_2$, —C$_1$-C$_6$alkyl, —OC$_1$-C$_6$alkyl, —SC$_1$-C$_6$alkyl, —S(O)$_2$C$_1$-C$_6$alkyl, —N(R$^6$)(R$^6$), —N(R$^6$)C(=O)C$_1$-C$_6$alkyl, —N(R$^6$)S(O)$_2$C$_1$-C$_6$alkyl, —C(=O)H, —C(=O)OH, —C(=O)OC$_1$-C$_6$alkyl, —C(=O)C$_1$-C$_6$alkyl, —C(=O)N(R$^6$)(R$^6$), PhenylCH=CHC(=O)—, PhenylC(=O)CH=CH—, —C(=O)Phenyl, —C(=O)Naphthyl, —C(=O)Heterocycle, Heterocycle, Heteroaryl, C$_3$-C$_7$Cycloalkyl, Phenyl and Naphthyl;
wherein —C$_1$-C$_6$alkyl and the alkyl groups of —OC$_1$-C$_6$alkyl, —SC$_1$-C$_6$alkyl, —S(O)$_2$C$_1$-C$_6$alkyl, —N(R$^6$)C(=O)C$_1$-C$_6$alkyl, —N(R$^6$)S(O)$_2$C$_1$-C$_6$alkyl, —C(=O)OC$_1$-C$_6$alkyl, and —C(=O)C$_1$-C$_6$alkyl are optionally substituted with 1-5 halogens and optionally substituted with 1-2 groups independently selected from —OH, —OC$_1$-C$_3$alkyl optionally substituted with 1-5 halogens, —S(O)$_2$C$_1$-C$_3$alkyl, —C(=O)C$_1$-C$_3$alkyl, —OC(=O)C$_1$-C$_3$alkyl, —NHC(=O)CH$_3$, —NHC(=O)OC$_1$-C$_6$alkyl, —NHS(O)$_2$CH$_3$, —N(R$^6$)(R$^6$), Heterocycle, Heteroaryl, C$_3$-C$_7$Cycloalkyl, Phenyl, and Naphthyl;
wherein Phenyl of PhenylCH=CHC(=O)—, Phenyl of PhenylC(=O)CH=CH—, —C(=O)Phenyl, —C(=O)Naphthyl, —C(=O)Heterocycle, Heterocycle, Heteroaryl, C$_3$-C$_7$Cycloalkyl, Phenyl and Naphthyl either as R$^1$, R$^2$, R$^3$, R$^4$, and R$^5$ or as substituents on R$^1$, R$^2$, R$^3$, R$^4$, and R$^5$ are optionally substituted with 1-4 substituents independently selected from halogen, —CN, —NO$_2$, —OH, —C$_1$-C$_3$alkyl, —C(=O)C$_1$-C$_3$alkyl, —S(O)$_2$C$_1$-C$_3$alkyl, and —OC$_1$-C$_3$alkyl, wherein the —C$_1$-C$_3$alkyl, —OC$_1$-C$_3$alkyl, —S(O)$_2$C$_1$-C$_3$alkyl, and —C(=O)C$_1$-C$_3$alkyl substituents are optionally substituted with 1-5 halogens;
wherein optionally the pair of substituents R$^1$ and R$^2$ together represent a 3- or 4-carbon bridging group selected from —CH$_2$CH$_2$CH$_2$—, —CH$_2$CH$_2$CH$_2$CH$_2$—, and —CH=CH—CH=CH—, forming a fused cyclopentyl, cyclohexyl, or phenyl ring at the R$^1$ and R$^2$ positions, wherein said bridging group is optionally substituted with 1-3 groups independently selected from halogen, —OH, —CN, —NO$_2$, —C$_1$-C$_3$alkyl, —OC$_1$-C$_3$alkyl, —SC$_1$-C$_3$alkyl, —S(O)$_2$C$_1$-C$_3$alkyl, —CF$_3$, and —OCF$_3$;
Each R$^6$ is independently selected from the group consisting of H and —C$_1$-C$_6$alkyl;

R⁷ is selected from the group consisting of H and —C₁-C₃alkyl;

R⁸ is selected from the group consisting of H, —OH, —C₁-C₃alkyl optionally substituted with 1-3 halogens, and —OC₁-C₃alkyl optionally substituted with 1-3 halogens and optionally with one group —C(═O)OR¹⁰; and R⁹ and R¹⁰ are independently selected from the group consisting of H and —C₁-C₆alkyl, wherein —C₁-C₆alkyl is optionally substituted with 1-5 halogens.

2. The compound of claim 1, or a pharmaceutically acceptable salt thereof, wherein R¹, R², R³, R⁴, and R⁵ are independently selected from (1) H; (2) halogen; (3) —NO₂; (4) —CN; (5) —C₁₋₆alkyl, which is optionally substituted with 1-5 halogens and optionally substituted with 1-2 substituents independently selected from —OH, —C(═O)C₁-C₃alkyl, and —OC₁₋₃alkyl which is optionally substituted with 1-3 halogens; (6) —OC₁₋₆alkyl, which is optionally substituted with 1-5 halogens and optionally with one Phenyl; (7) —C(═O)C₁-C₃alkyl, which is optionally substituted with 1-5 halogens; (8) —N(R⁶)(R⁶); (9) —C(═O)N(R⁶)(R⁶); (10) —C(═O)OC₁-C₃alkyl; (11) —S(O)₂C₁-C₃alkyl; (12) Phenyl; (13) PhenylCH═CHC(═O)—; and (14) PhenylC(═O)CH═CH—; wherein Phenyl in all uses is optionally substituted with 1-3 groups independently selected from halogen, CH₃, CF₃, —OCH₃, and —OCF₃; and Each R⁶ is independently selected from the group consisting of H and —C₁-C₃alkyl;

wherein optionally R¹ and R² together represent the 4-carbon chain —CH═CH—CH═CH—, forming a fused phenyl ring at the R¹ and R² positions, wherein said fused phenyl ring is optionally substituted with 1-3 substituents independently selected from halogen, —OH, —CN, —NO₂, —C₁-C₃alkyl, —OC₁-C₃alkyl, —SC₁-C₃alkyl, —S(O)₂C₁-C₃alkyl, —CF₃, and —OCF₃.

3. The compound of claim 1, or a pharmaceutically acceptable salt thereof, wherein R¹, R², R³, R⁴ and R⁵ are each independently selected from H, halogen, C₁-C₅alkyl optionally substituted with 1-5F, —OC₁-C₅alkyl optionally substituted with 1-5F, —CH₂OH, —CH(OH)CH₃, —CH(OH)CF₃, —C(═O)H, —C(═O)CH₃, —CN, —NO₂, Phenyl, —OCH₂Phenyl, —C(═O)OC₁-C₃alkyl, —S(O)₂CH₃, —C(═O)N(R⁶)(R⁶), —N(R₆)(R₆), PhenylCH═CHC(═O)—, and PhenylC(═O)CH═CH—, wherein Phenyl in each instance is optionally substituted with 1-3 groups independently selected from halogen, CH₃, CF₃, —OCH₃, and —OCF₃;

Each R⁶ is independently selected from H and CH₃;

wherein optionally R¹ and R² together represent the 4-carbon chain —CH═CH—CH═CH—, forming a fused phenyl ring at the R¹ and R² positions, wherein said fused phenyl ring is optionally substituted with 1-2 substituents independently selected from halogen, —C₁-C₃alkyl, —OC₁-C₃alkyl, —CF₃, and —OCF₃.

4. The compound of claim 1, wherein each R⁶ is independently selected from H and CH₃.

5. The compound of claim 1, or a pharmaceutically acceptable salt thereof, wherein R¹ and R² together represent the 4-carbon chain —CH═CH—CH═CH—, forming a fused phenyl ring at the R¹ and R² positions, wherein said fused phenyl ring is optionally substituted with 1-3 substituents independently selected from halogen, —OH, —CN, —NO₂, —C₁-C₃alkyl, —OC₁-C₃alkyl, —SC₁-C₃alkyl, —S(O)₂C₁-C₃alkyl, —CF₃, and —OCF₃.

6. The compound of claim 5, or a pharmaceutically acceptable salt thereof, wherein said fused phenyl ring is optionally substituted with 1-2 substituents independently selected from halogen, —C₁-C₃alkyl, —OC₁-C₃alkyl, —CF₃, and —OCF₃.

7. The compound of claim 1, or a pharmaceutically acceptable salt thereof, wherein A is selected from the group consisting of —CH₂—, —CF₂—, —O—, —N(R⁶)—, —S—, —S(O)—, —S(O)₂—, —C(═O)—, and —CH(OH)—; and B is selected from the group consisting of —CH₂—, —CH₂CH₂—, and —CH(CH₃)—;

or alternatively -A-B- is selected from the group consisting of —N(R⁶)C(═O)—, —C(═O)N(R⁶)—,

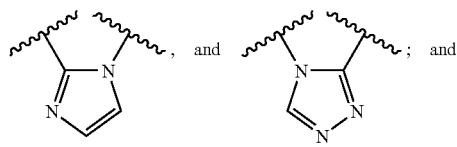
, and ; and

Each R⁶ is independently selected from H and CH₃.

8. The compound of claim 1, or a pharmaceutically acceptable salt thereof, wherein A is selected from the group consisting of —CH₂—, —O—, —S—, —S(O)₂—, —C(═O)—, and —CH(OH)—; and B is selected from the group consisting of —CH₂—, —CH₂CH₂—, and —CH(CH₃)—;

or alternatively -A-B- is selected from the group consisting of —N(R⁶)C(═O)—, —C(═O)N(R⁶)—,

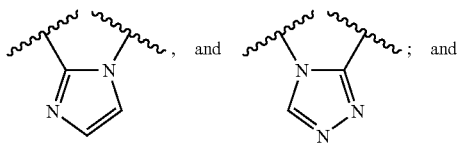
, and ; and

Each R⁶ is independently selected from H and CH₃.

9. The compound of claim 1, or a pharmaceutically acceptable salt thereof, wherein Z is —CR⁷R⁸CO₂H;

R⁷ is H;

R⁸ is selected from the group consisting of H, —OH, CH₃, and —OCH₂C(═O)OR¹⁰; and R¹⁰ is selected from the group consisting of H and —C₁-C₄alkyl.

10. The compound of claim 1, or a pharmaceutically acceptable salt thereof, wherein A is selected from the group consisting of —CH₂—, —O—, —S—, —S(O)₂—, —C(═O)—, and —CH(OH)—; and B is selected from the group consisting of —CH₂—, —CH₂CH₂—, and —CH(CH₃)—;

or alternatively -A-B- is selected from the group consisting of —N(R⁶)C(═O)—, —C(═O)N(R⁶)—,

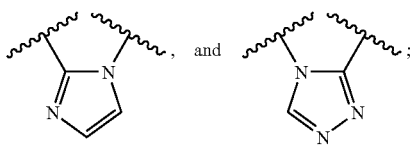
, and ;

wherein R¹ is selected from the group consisting of H, halogen, C₁-C₅alkyl optionally substituted with 1-5F, —OC₁-C₅alkyl optionally substituted with 1-5F, —CH₂OH, —CH(OH)CH₃, —CH(OH)CF₃, —C(═O)H, —C(═O)CH₃, —CN, —NO₂, —C(═O)OCH₃, —S(O)$_2$CH$_3$, —C(=O)N(R$^6$)(R$^6$), —N(R$_6$)(R$_6$), and —OCH$_2$Phenyl in which Phenyl is optionally substituted with 1-3 groups independently selected from halogen, CH$_3$, CF$_3$, —OCH$_3$, and —OCF$_3$;

R$^2$ is selected from the group consisting of H, halogen, C$_1$-C$_3$alkyl optionally substituted with 1-3F, —OC$_1$-C$_3$alkyl optionally substituted with 1-3F, and Phenyl optionally substituted with 1-3 groups independently selected from halogen, CH$_3$, CF$_3$, —OCH$_3$, and —OCF$_3$;

R$^3$ is selected from the group consisting of H, halogen, CH$_3$, CF$_3$, —OCH$_3$, and —OCF$_3$;

R$^4$ is selected from the group consisting of H, halogen, CH$_3$, CF$_3$, —OCH$_3$, —OCF$_3$, C(=O)H, —C(=O)CH$_3$, —C(=O)OCH$_3$, —C(=O)N(R$^6$)(R$^6$), —CN, —NO$_2$, PhenylCH=CHC(=O)—, and PhenylC(=O)CH=CH—, wherein Phenyl in each instance is optionally substituted with 1-3 groups independently selected from halogen, CH$_3$, CF$_3$, —OCH$_3$, and —OCF$_3$;

R$^5$ is H;

Each R$^6$ is independently selected from H and CH$_3$;

wherein optionally R$^1$ and R$^2$ together represent the 4-carbon chain —CH=CH—CH=CH—, forming a fused phenyl ring at the R$^1$ and R$^2$ positions, wherein said fused phenyl ring is optionally substituted with 1-2 substituents independently selected from halogen, —C$_1$-C$_3$alkyl, —OC$_1$-C$_3$alkyl, —CF$_3$, and —OCF$_3$;

Z is —CR$^7$R$^8$CO$_2$H;

R$^7$ is H;

R$^8$ is selected from the group consisting of H, —OH, CH$_3$, and —OCH$_2$C(=O)OR$^{10}$; and R$^{10}$ is selected from the group consisting of H and —C$_1$-C$_4$alkyl.

11. The compound of claim 10, which is selected from the group consisting of the compounds below, or a pharmaceutically acceptable salt thereof:

| Ex. | Structures |
|---|---|
| 1 | |
| 2 | |
| 3 | |
| 4 | 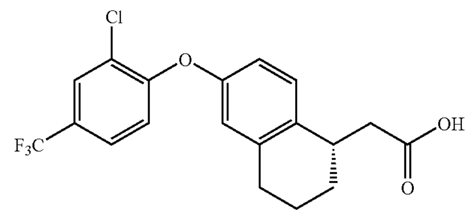 |
| 5 | 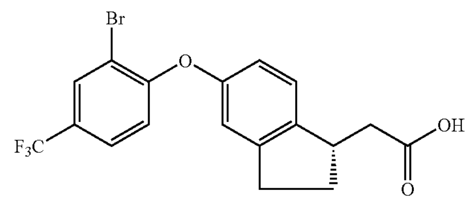 |
| 6 | 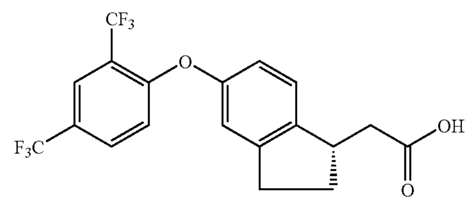 |
| 7 | 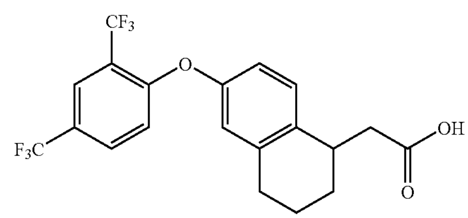 |
| 8 | 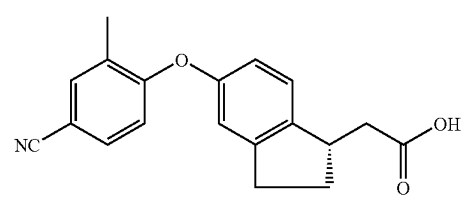 |
| 9 | 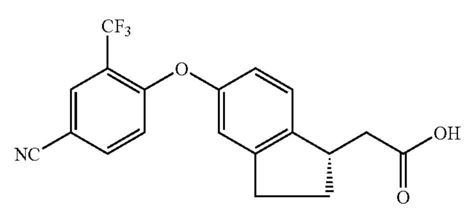 |
| 10 | 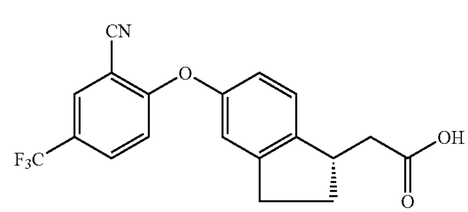 |

75
-continued
| Ex. | Structures |
|---|---|
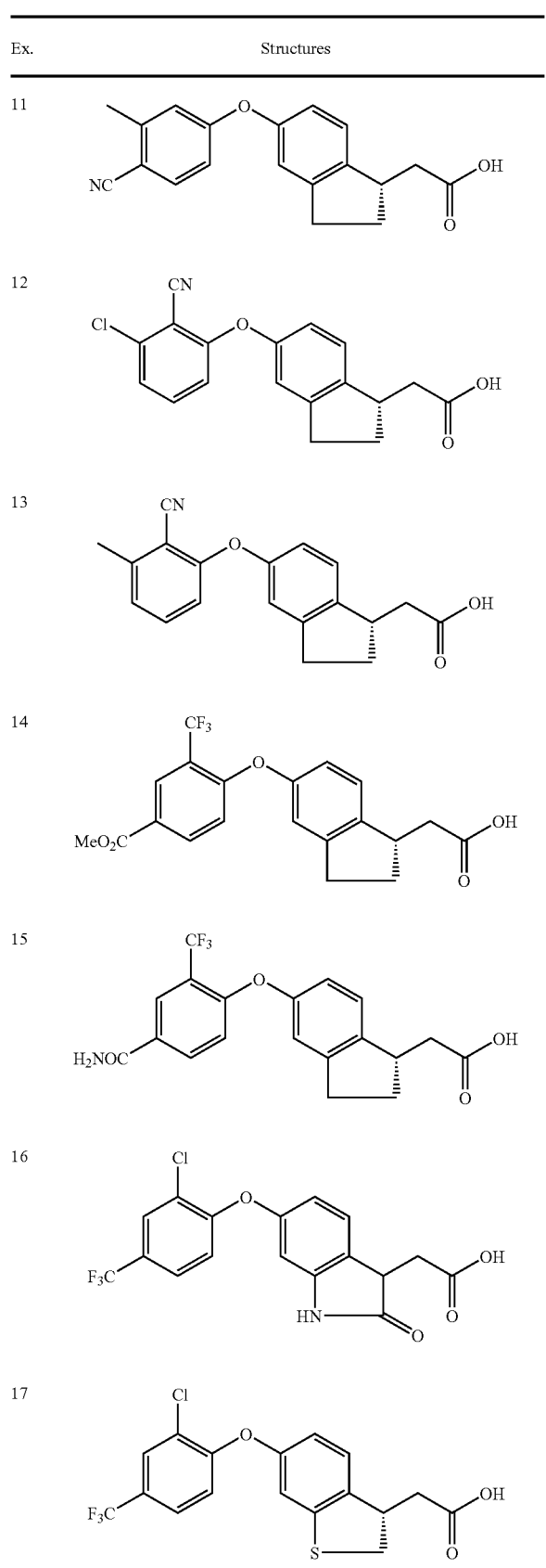
76
-continued
| Ex. | Structures |
|---|---|
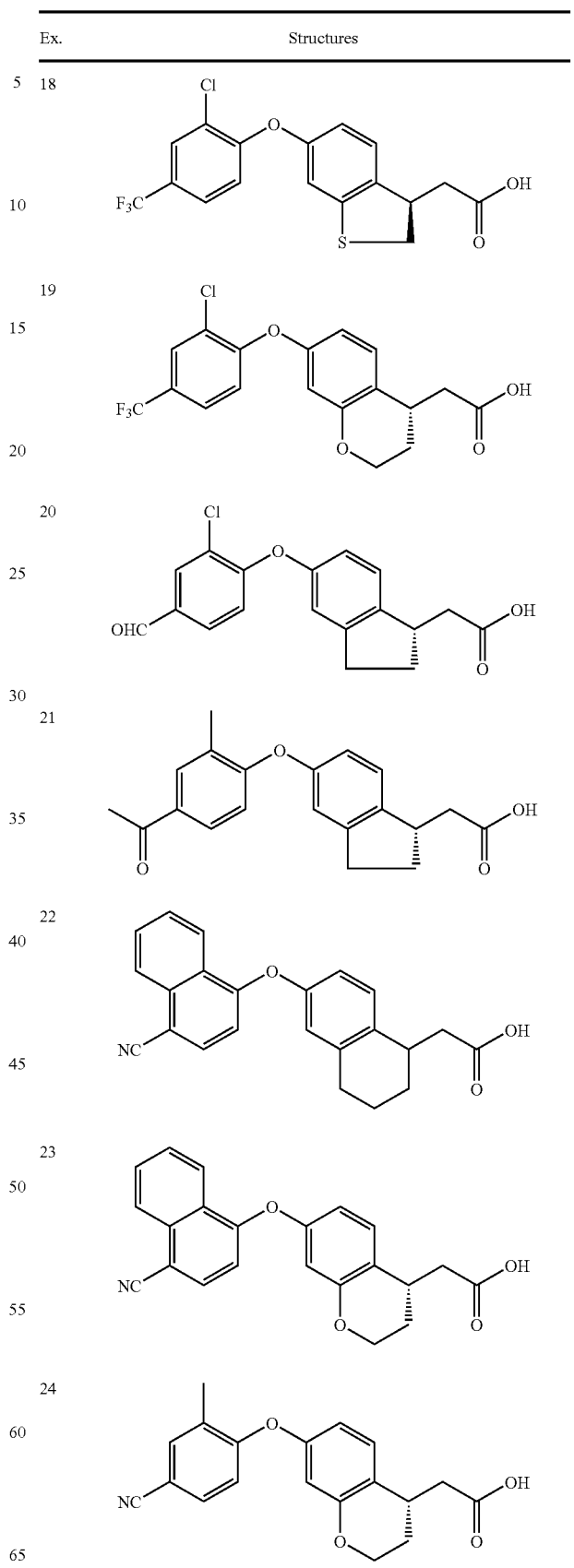

| Ex. | Structures |
|---|---|
| 25 | (2-chloro-4-cyanophenoxy attached to chroman-4-yl acetic acid) |
| 26 | (4-cyano-3,5-dimethylphenoxy attached to chroman-4-yl acetic acid) |
| 27 | (3-chloro-4-carbamoylphenoxy attached to indan-1-yl acetic acid) |
| 28 | (2-methoxy-4-trifluoromethylphenoxy attached to indan-1-yl acetic acid) |
| 29 | (2-methoxy-4-trifluoromethylphenoxy attached to chroman-4-yl acetic acid) |
| 30 | (2-methyl-4-trifluoromethylphenoxy attached to chroman-4-yl acetic acid) |
| 31 | (2-acetyl-4-trifluoromethylphenoxy attached to chroman-4-yl acetic acid) |

| Ex. | Structures |
|---|---|
| 32 | (2-formyl-5-trifluoromethylphenoxy attached to chroman-4-yl acetic acid) |
| 33 | (2-acetyl-4-trifluoromethylphenoxy attached to indan-1-yl acetic acid) |
| 34 | (4-acetylnaphthalen-1-yloxy attached to chroman-4-yl acetic acid) |
| 35 | (phenoxy attached to indan-1-yl acetic acid) |
| 36 | (2-chlorophenoxy attached to indan-1-yl acetic acid) |
| 37 | (4-cyanonaphthalen-1-yloxy attached to indan-1-yl acetic acid) |
| 38 | (2-methyl-4-trifluoromethylphenoxy attached to indan-1-yl acetic acid) |

| Ex. | Structures |
|---|---|
| 39 | 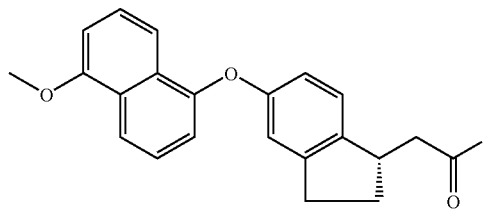 |
| 40 | 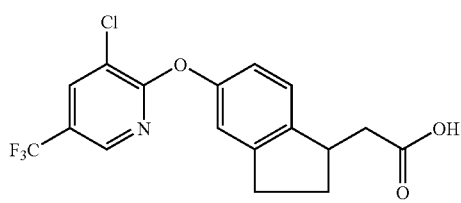 |
| 41 | 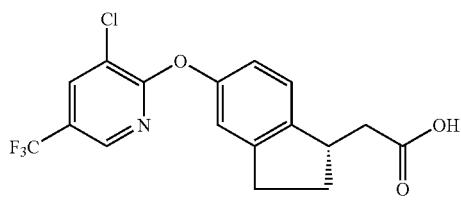 |
| 42 | 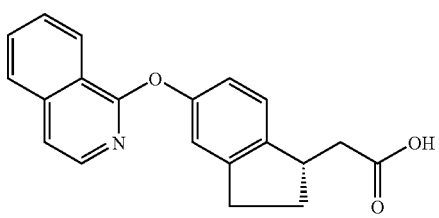 |
| 43 | 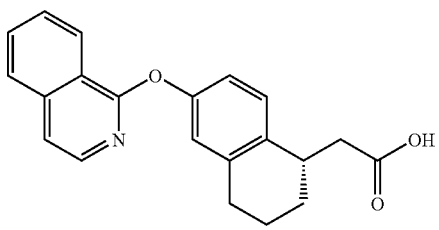 |
| 44 | 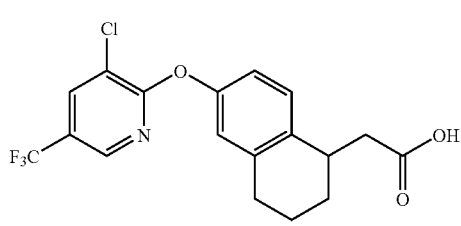 |
| 45 | 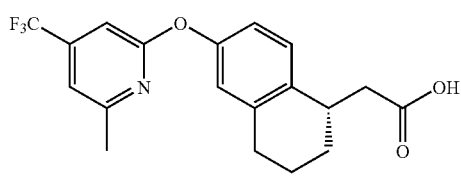 |
| Ex. | Structures |
|---|---|
| 46 | 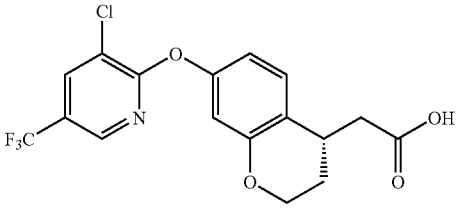 |
| 47 | 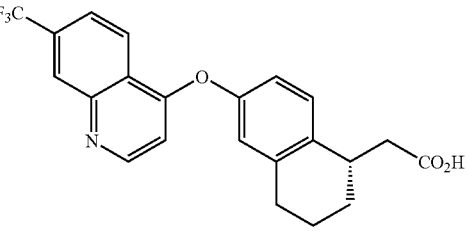 |
| 48 | 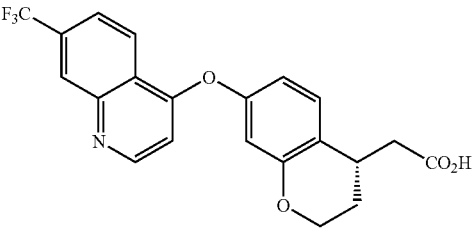 |
| 49 | 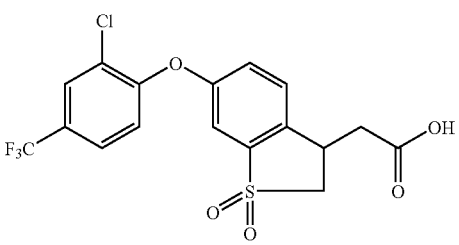 |
| 50 | 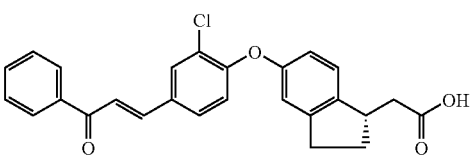 |
| 51 | 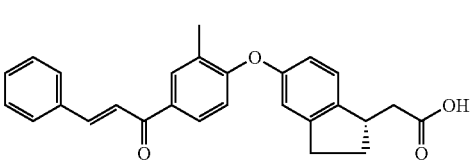 |
| 52 | 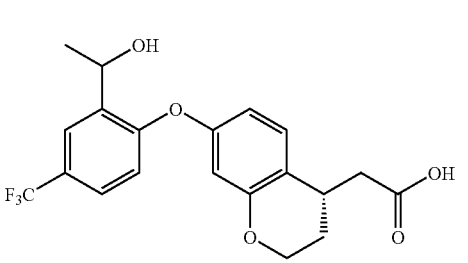 |

-continued

| Ex. | Structures |
|---|---|
| 53 | 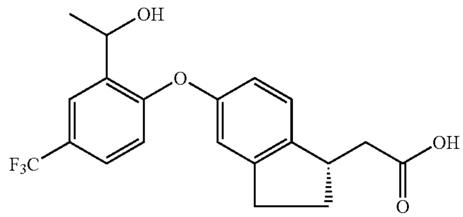 |
| 54 | 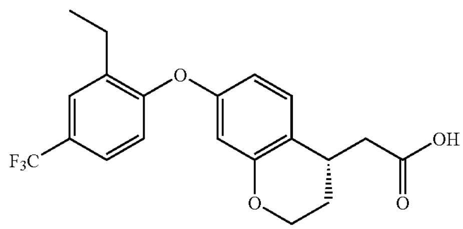 |
| 54A | 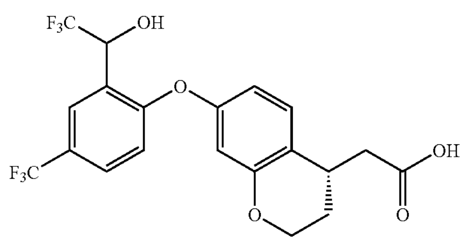 |
| 54B | 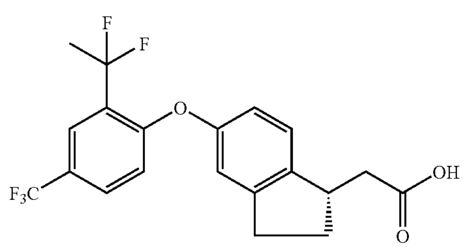 |
| 55 | 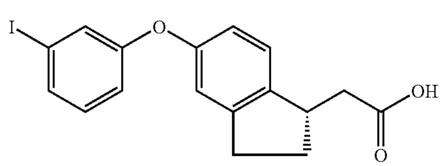 |
| 56 | 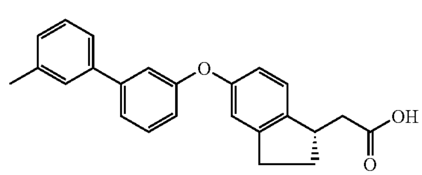 |
| 57 | 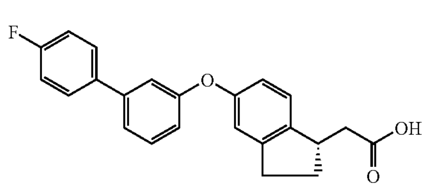 |

-continued

| Ex. | Structures |
|---|---|
| 58 | 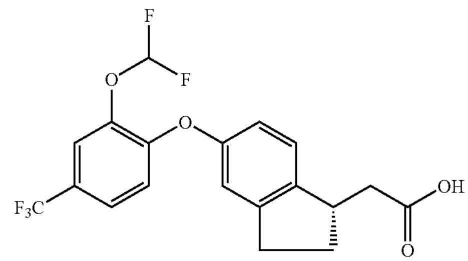 |
| 59 | 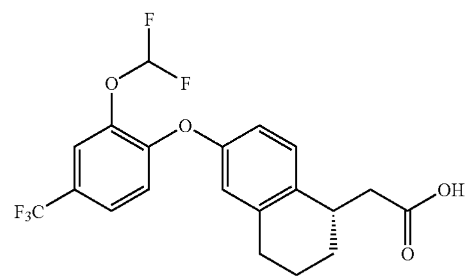 |
| 60 | 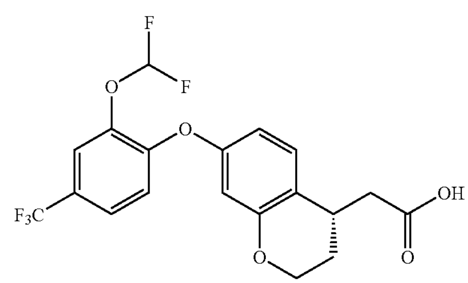 |
| 61 | 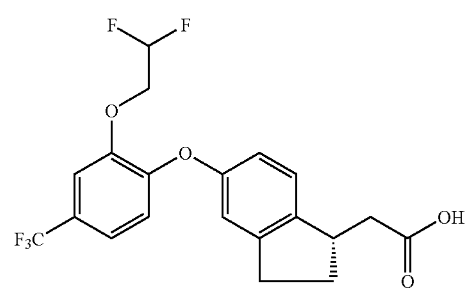 |
| 62 | 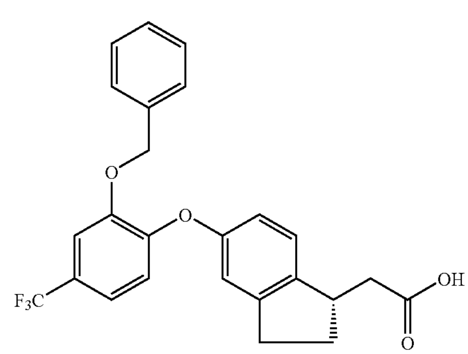 |

| Ex. | Structures |
|---|---|
| 63 | 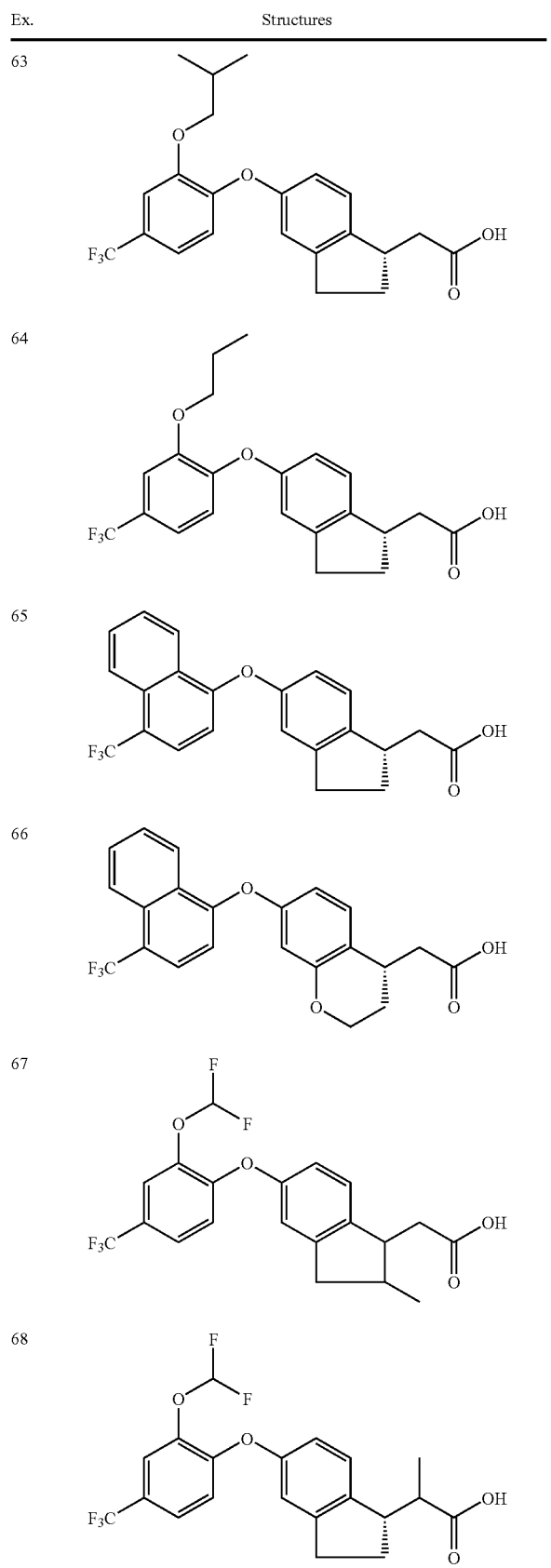 |
| 64 | |
| 65 | |
| 66 | |
| 67 | |
| 68 | |
| Ex. | Structures |
|---|---|
| 69 | 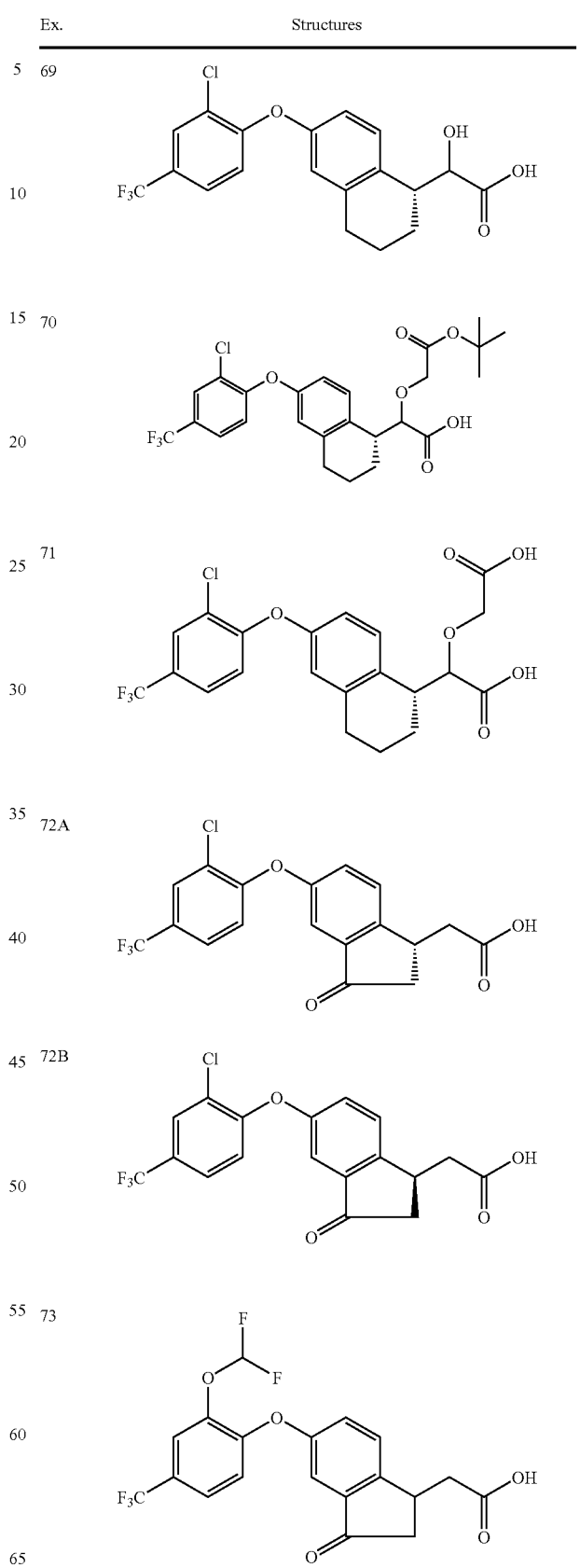 |
| 70 | |
| 71 | |
| 72A | |
| 72B | |
| 73 | |

| Ex. | Structures |
|---|---|
| 74 | 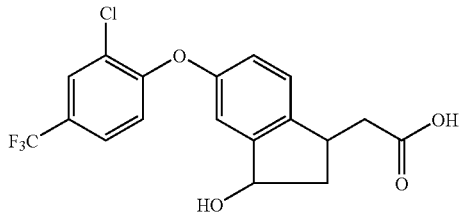 |
| 75 | 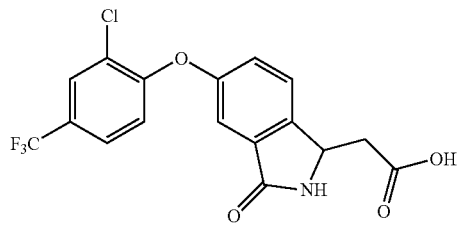 |
| 76 | 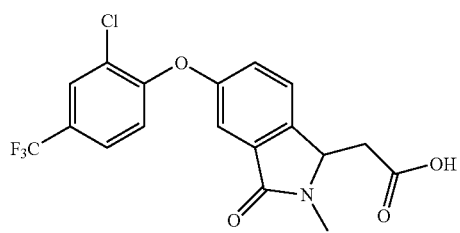 |
| 77 | 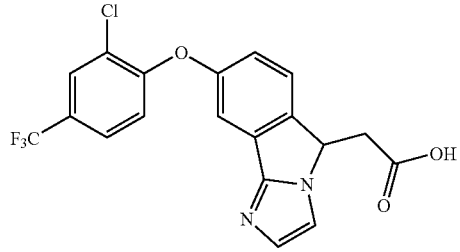 |
| 78 | 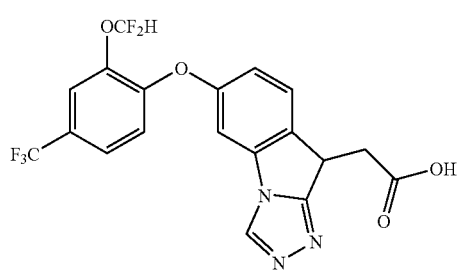 |
| 79 | 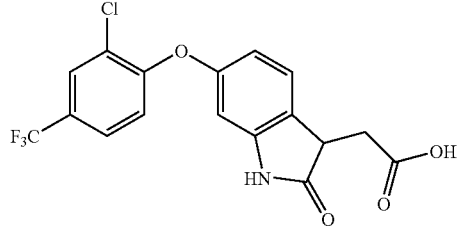 |

| Ex. | Structures |
|---|---|
| 48A | 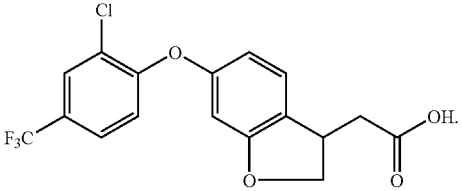 |

12. A pharmaceutical composition comprising the compound of claim 1, or a pharmaceutically acceptable salt thereof, and a pharmaceutically acceptable carrier.

13. A method of treating type 2 diabetes mellitus in a patient in need of treatment comprising the administration to the patient of a therapeutically effective amount of the compound of formula I, or a pharmaceutically acceptable salt thereof.

14. A pharmaceutical composition comprising
  (1) the compound of claim 1, or a pharmaceutically acceptable salt thereof;
  (2) one or more compounds selected from the group consisting of:
    (a) PPAR gamma agonists and partial agonists;
    (b) biguanides;
    (c) protein tyrosine phosphatase-1B (PTP-1B) inhibitors;
    (d) dipeptidyl peptidase IV (DP-IV) inhibitors;
    (e) insulin or an insulin mimetic;
    (f) sulfonylureas;
    (g) α-glucosidase inhibitors;
    (h) agents which improve a patient's lipid profile, said agents being selected from the group consisting of (i) HMG-CoA reductase inhibitors, (ii) bile acid sequestrants, (iii) nicotinyl alcohol, nicotinic acid or a salt thereof, (iv) PPARα agonists, (v) cholesterol absorption inhibitors, (vi) acyl CoA:cholesterol acyltransferase (ACAT) inhibitors, (vii) CETP inhibitors, and (viii) phenolic anti-oxidants;
    (i) PPARα/γ dual agonists,
    (j) PPARδ agonists,
    (k) antiobesity compounds,
    (l) ileal bile acid transporter inhibitors;
    (m) anti-inflammatory agents;
    (n) glucagon receptor antagonists;
    (o) GLP-1;
    (p) GIP-1;
    (q) GLP-1 analogs;
    (r) Glucokinase activators;
    (s) GPR 119 agonists;
    (t) GPR120 agonists; and
    (u) Hydroxysterol dehydrogenase-1 (HSD-1) inhibitors; and
  (3) a pharmaceutically acceptable carrier.

* * * * *